United States Patent
Aldwinckle et al.

[11] Patent Number: 5,824,861
[45] Date of Patent: Oct. 20, 1998

[54] TRANSGENIC POMACEOUS FRUIT WITH FIRE BLIGHT RESISTANCE

[75] Inventors: Herbert S. Aldwinckle, Geneva; John L. Norelli, Ithaca, both of N.Y.

[73] Assignee: Cornell Research Foundation, Inc., Ithaca, N.Y.

[21] Appl. No.: 385,590

[22] Filed: Feb. 8, 1995

Related U.S. Application Data

[63] Continuation of Ser. No. 33,772, Mar. 18, 1993, abandoned, which is a continuation-in-part of Ser. No. 954,347, Sep. 30, 1992, abandoned.

[51] Int. Cl.$^6$ .............................. A01H 1/04; C12N 5/00; C12N 15/00
[52] U.S. Cl. ................................ 800/205; 800/DIG. 65; 435/172.3
[58] Field of Search ........................... 800/205, DIG. 65; 435/172.3, 240.4, 320.1; 536/23.2, 23.5, 24.1; 935/52, 55, 67

[56] References Cited

U.S. PATENT DOCUMENTS

| | | | |
|---|---|---|---|
| 4,945,050 | 7/1990 | Sanford et al. | 435/172.1 |
| 5,036,006 | 7/1991 | Sanford et al. | 435/170.1 |
| 5,100,792 | 3/1992 | Sanford et al. | 435/172.1 |

FOREIGN PATENT DOCUMENTS

| | | |
|---|---|---|
| 1321157 | 8/1993 | Canada . |
| 182106 | 10/1985 | European Pat. Off. . |
| 219009 | 10/1986 | European Pat. Off. . |
| 299828 | 6/1988 | European Pat. Off. . |
| WO 89/04371 | 5/1989 | European Pat. Off. . |
| 237387 | 7/1992 | New Zealand . |
| 89/04371 | 5/1989 | WIPO . |

OTHER PUBLICATIONS

K. Düring, et al., "Antibacterial Resistance of Transgenic Potato Plants Producing T4 Lysozyme," *Dev. Plant Pathol.* 2:437:40 (1993).

D.J. James, et al., "Progress in the Introduction of Transgenes for Pest Resistance in Apples and Strawberries," *Phytoparasitica* 20:83S–87S (1992).

A.M. Dandekar, "Engineering for Apple and Walnut Resistance to Codling Moth," *Brighton Crop Prot. Conf.—Pest Dis.* 2:741–7 (1992).

J. James, et al., "Synthetic Genes Make Better Potatoes," *New Scientist*, vol. 17, (1987).

J. James, et al., "Increasing Bacterial Disease Resistance in Plants Utilizing Antibacterial Genes From Insects," *BioEssays* 6:263–270 (1987).

S. Jia, et al., "Genetic Engineering of Chinese Potato Cultivars by Introducing Antibacterial Polypeptide Gene," *Proceeding of the Asia–Pacific Conference on Agricultural Biotechnology*, 1992.

L. Destefano–Beltran, et al., "Enhancing Bacterial and Fungal Disease Resistance in Plants: Application to Potato," *The Molecular and Cellular Biology of the Potato* Vayda, M.E. and Park, W.D. (eds.) CAB International, Wallingford, U.K. pp. 205–221 (1990).

D.J. James, et al., "Genetic Transformation of Apple *Malus–Pumila* Mill.) Using a Disarmed Ti–Binary–Vector," *Plant Cell Reports*, 7:658–61 (1989).

(List continued on next page.)

*Primary Examiner*—Bruce R. Campbell
*Attorney, Agent, or Firm*—Nixon, Hargrave, Devans & Doyle

[57] ABSTRACT

The present invention relates to a method of conferring resistance against fire blight to pomaceous fruit scion or rootstock cultivars by transforming such cultivars with a gene which encodes for lytic proteins. Such transformation can be effected by bacterial infection or propulsion of particles into cell interiors. Once transformation has taken place, the cultivar is regenerated to a transgenic pomaceous fruit tree. This technique is particularly useful in treating apple and pear cultivars.

25 Claims, 15 Drawing Sheets

OTHER PUBLICATIONS

T. Van Der Swet, et al., "Fire Blight—A Bacterial Disease of Rosaceous Plants," *Agricultural Hanbook No. 510*, (1979).

H.S. Aldwinckle, et al., "Fire Blight and Its Control," *Horticultural Reviews*, vol. 1, (1978).

Destafano–Beltran, et al., "The introduction into tobacco plants of genes which encode some of the humoral immune response of *Hyalophora cecropia*," (1992).

Jurgen Denecke, et al., "Protein Secretion in Plant Cells Can Occur via a Default Pathway," *The Plant Cell*, vol. 2, pp. 51–59, (1990).

J.M. Jaynes, et al., Expression of a Cecropin B Lytic Peptide Analog in Transgenic Tobacco Confers Enhanced Resistance to Bacterial Wilt Caused by *Pseudomonas solanacearum, Plant Science* 89:43–53 (Apr. 1993).

```
AGTCCCGCTGTGTGTACGACACTGGCAACATGAGGTCTTTGCTAATCTTG
                                ▸MetArgSerLeuLeuIleLeu
                                         -18
GTGCTTTGCTTCCTGCCCCTGGCTGCTCTGGGGAAAGTCTTTGGACGATG
▸ValLeuCysPheLeuProLeuAlaAlaLeuGlyLysValPheGlyArgCy
     -10                                -1 1
TGAGCTGGCAGCGGCTATGAAGCGTCACGGACTTGATAACTATCGGGGAT
▸sGluLeuAlaAlaAlaMetLysArgHisGlyLeuAspAsnTyrArgGlyT
           10                          20
ACAGCCTGGGAAACTGGGTGTGTGTTGCAAAATTCGAGAGTAACTTCAAC
▸yrSerLeuGlyAsnTrpValCysValAlaLysPheGluSerAsnPheAsn
                      30
ACCCAGGCTACAAACCGTAACACCGATGGGAGTACCGACTACGGAATCCT
▸ThrGlnAlaThrAsnArgAsnThrAspGlySerThrAspTyrGlyIleLe
    40                                 50
ACAGATCAACAGCCGCTGGTGGTGCAACGATGGCAGGACCCCAGGCTCCA
▸uGlnIleAsnSerArgTrpTrpCysAsnAspGlyArgThrProGlySerA
              60                              70
GGAACCTGTGCAACATCCCGTGCTCAGCCCTGCTGAGCTCAGACATAACA
▸rgAsnLeuCysAsnIleProCysSerAlaLeuLeuSerSerAspIleThr
                              80
GCGAGCGTGAACTGCGCGAAGAAGATCGTCAGCGATGGAAACGGCATGAG
▸AlaSerValAsnCysAlaLysLysIleValSerAspGlyAsnGlyMetSe
      90                              100
CGCGTGGGTCGCCTGGCGCAACCGCTGCAAGGGTACCGACGTCCAGGCGT
▸rAlaTrpValAlaTrpArgAsnArgCysLysGlyThrAspValGlnAlaT
              110                             120
GGATCAGAGGCTGCCGGCTGTGAGGAGCTGCCGCACCCGGCCCGCCCGCT
▸rpIleArgGlyCysArgLeu
                          129 STOP
GCACAGCCGGCCGCTTTGCGAGCGCGACGCTACCCGCTTGGCAGTTTTAA
ACGCATCCCTCATTAAAACGACTATACGCAAACGCC
```

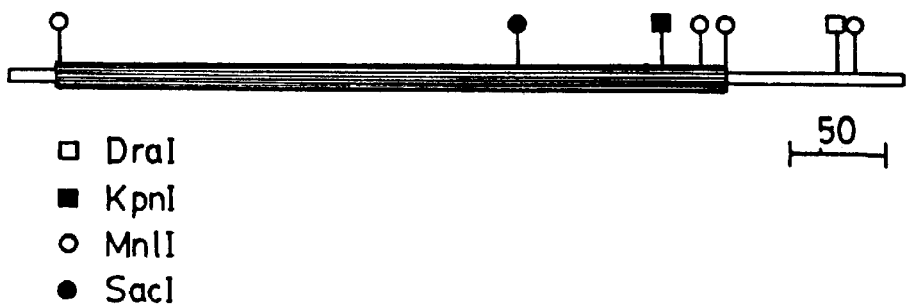

□ DraI
■ KpnI
○ MnlI
● SacI

FIG.1

SUBCLONE HindIII FRAGMENT INTO pBI121 AND SELECT FOR CLOCK-WISE ORIENTATION WITH RESPECT TO NPTII AND GUS GENES TO YIELD pLDB11

SUBCLONE HindIII FRAGMENT INTO pBI121 AND SELECT FOR CLOCK-WISE ORIENTATION WITH RESPECT TO NPTII AND GUS GENES TO YIELD pLDB12

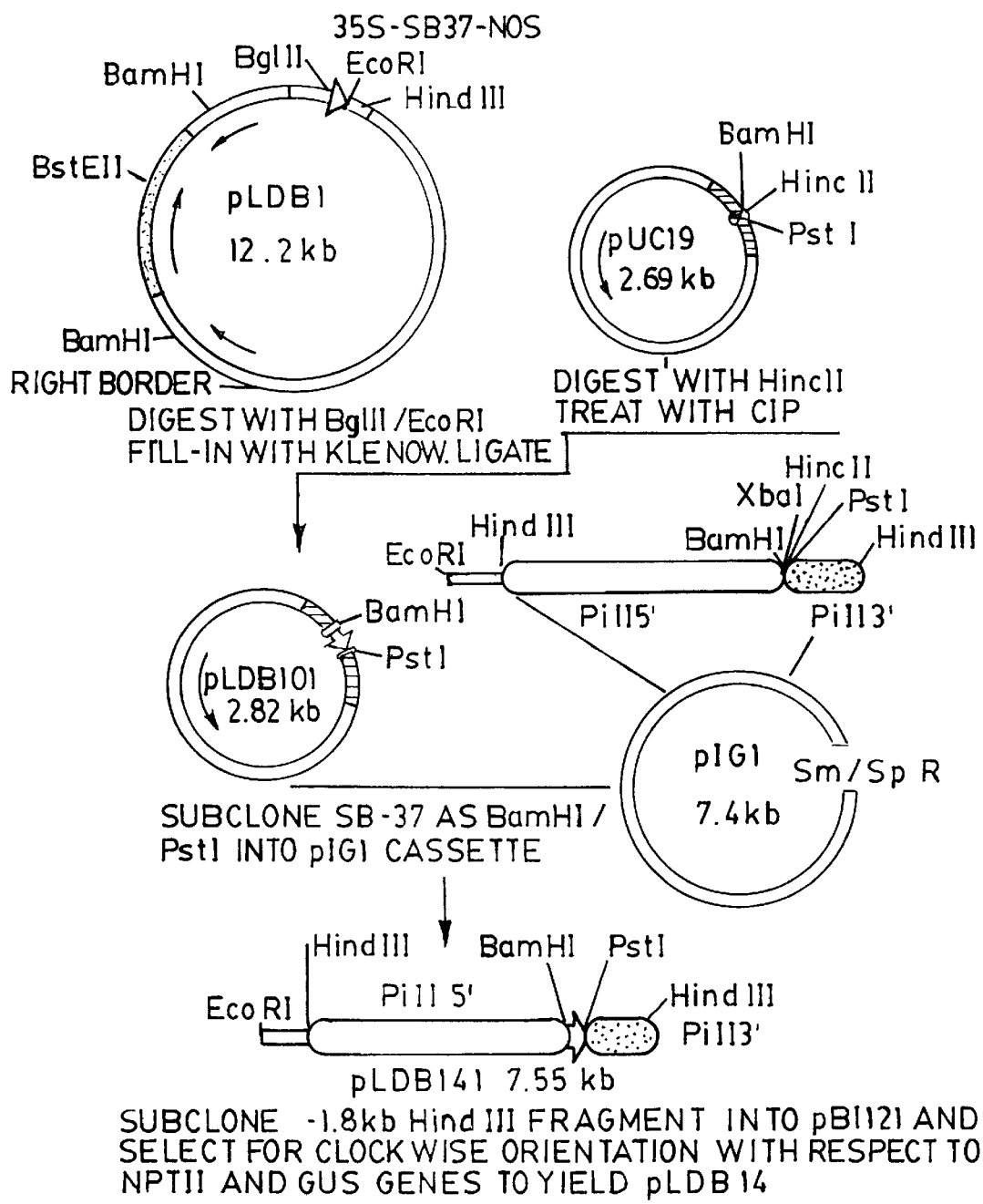
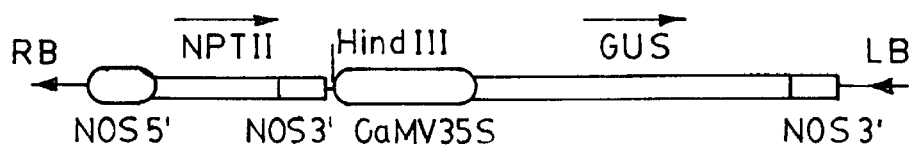
FIG. 12

```
GACGCGCACGGAGCCCTTACGCTCAACTCCGATGGTACCTCTGGTGCTGTGGTTAAA
▶AspAlaHisGlyAlaLeuThrLeuAsnSerAspGlyThrSerGlyAlaValValLys
           10                         20
GTACCCTTTGCTGGTAACGACAAGAATATAGTAAGCGCTATCGGTTCCGTAGACTTA
▶ValProPheAlaGlyAsnAspLysAsnIleValSerAlaIleGlySerValAspLeu
           30                         40
ACTGATAGGCAGAAACTAGGCGCTGCAACCGCTGGAGTGGCACTGGATAATATAAAC
▶ThrAspArgGlnLysLeuGlyAlaAlaThrAlaGlyValAlaLeuAspAsnIleAsn
           50                         60
GGTCACGGACTAAGTCTCACGGATACACACATCCCCGGGTTCGGAGACAAGATGACA
▶GlyHisGlyLeuSerLeuThrAspThrHisIleProGlyPheGlyAspLysMetThr
           70                         80
GCAGCCGGCAAAGTGAATGTCTTCCACAATGATAACCACGACATCACAGCGAAGGCT
▶AlaAlaGlyLysValAsnValPheHisAsnAspAsnHisAspIleThrAlaLysAla
           90                        100
TTCGCCACCAGAAACATGCCGGATATTGCTAATGTACCTAATTTCAACACTGTCGGT
▶PheAlaThrArgAsnMetProAspIleAlaAsnValProAsnPheAsnThrValGly
          110
GGCGGAATAGACTATATGTTCAAAGATAAGATTGGTGCATCTGCGAGCGCCGCTCAC
▶GlyGlyIleAspTyrMetPheLysAspLysIleGlyAlaSerAlaSerAlaAlaHis
          120                        130
ACGGACTTTATCAATCGCAACGACTACTCTCTTGACGGGAAACTGAACCTCTTCAAG
▶ThrAspPheIleAsnArgAsnAspTyrSerLeuAspGlyLysLeuAsnLeuPheLys
          140                        150
ACTCCTGATACCTCGATTGATTTCAACGCCGGTTTCAAGAAGTTCGATACACCTTTC
▶ThrProAspThrSerIleAspPheAsnAlaGlyPheLysLysPheAspThrProPhe
          160                        170
ATGAAGTCCTCTTGGGAGCCTAACTTCGGATTCTCACTTTCTAAATATTTCTGATTA
▶MetLysSerSerTrpGluProAsnPheGlyPheSerLeuSerLysTyrPhe
          180                   188 STOP
GTATTTAATTTTAATTCTATATATATAAATTTAGATGTATATGTATATATATATAT
TTTTTTTTATTAATATGATATCACTAAATGTATTTACTCCTTCGATTATTATTACT
TTTTTGTTTAAAGAAGTCCGCCTAATAAAGATAATTTG
```

■ BanII
◊ KpnI
□ AccI
○ SmaI
△ Eco RV
■ Dra I

FIG.13

*NON-TRANSGENIC LINE

TRANSGENIC POMACEOUS FRUIT WITH FIRE BLIGHT RESISTANCE

This application is a continuation of application Ser. No. 08/033,772, filed Mar. 18, 1993, abandoned, which is a continuation-in-part of U.S. patent application Ser. No. 07/954,347, filed Sep. 30, 1992, abandoned.

FIELD OF THE INVENTION

The present invention relates to conferring resistance against fire blight to pomaceous fruit scion and rootstock cultivars.

BACKGROUND OF THE INVENTION

In North America, trees for pomaceous fruits, such as apples, pears, quince, and other members of the Rosaceae family, are widely afflicted with the disease known as fire blight. Although indigenous to North America, this disease has more recently gained a foothold in Europe and now is of considerable concern on both sides of the Atlantic Ocean.

Fire blight is a bacterial disease caused by the infection of pomaceous fruit trees with the bacterium *Erwinia amylovora*. This bacterium can be disseminated from one tree to another by rain, wind, insects, birds, and man. Generally, infection occurs through natural openings in the tree, particularly blossoms. This causes blossoms first to appear water soaked, then to wilt and shrivel, and finally to turn black or brown. The disease then spreads to other parts of the tree, including branches, the trunk, and roots. This disease is manifested in tree limbs, trunks, and roots as cankers from which liquid oozes to spread the disease. Fire blight on twigs and suckers of fruit trees causes shoots, bark, and leaves to turn dark brown or black. This gives them a scorched appearance, hence the name fire blight.

Fire blight not only destroys the current year's crops but can also have a long-term impact. Blossom infection will reduce the current season's crop by killing fruit. In addition, twig blight destroys wood that could bear fruit spurs the following season. In pears and quinces, as well as many apple cultivars and rootstocks, blight can destroy large limbs or even an entire tree. In view of fire blight's potentially devastating effect on pomaceous fruit crops, the need exists to combat that disease.

It has been found that pear cultivars and many apple cultivars are particularly susceptible to fire blight. Nevertheless, both types of cultivars have some forms which are more resistant to fire blight. Not only do the fruiting scions have varying susceptibility, but so do the rootstocks for apple. One approach to combating fire blight is to breed cultivars and rootstocks for pomaceous fruit trees which are resistant to fire blight. Such programs, however, require trial and error and long periods of time to yield trees with fire blight resistance. In addition, a very limited number of apple and pear cultivars are responsible for a large portion of annual production. These cultivars are prized by consumers, supermarkets, and growers for their appearance, quality, flavor, storability, and production characteristics. To retain varietal characteristics and to introduce disease resistant genes by sexual breeding is virtually impossible, because the long generation time and self-incompatibility of apples and pears make backcross programs astronomically longterm and expensive.

Another approach to combating fire blight is by following horticultural practices which minimize the disease's outbreak. It has been found that reducing soil moisture and maintaining a balance of fertilizer nutrients can control fire blight infection and propagation. Although such approaches can be helpful, they are not capable of eliminating outbreak of the disease.

It is also possible to treat fire blight by removing cankers and blighted branches from infected trees, preferably during the winter when the disease is dormant. Equipment for carrying out such procedures must, however, be carefully sterilized to prevent the disease from being spread. Moreover, this approach cannot completely eradicate the disease, because areas with small cankers or internal infection may escape detection.

Trees infected with fire blight can also be periodically sprayed with copper compounds or antibiotics to control fire blight. The application of copper compounds has not achieved wide acceptance, however, because it is often ineffective and causes fruit russeting. The use of antibiotics, particularly streptomycin, is more effective and less injurious to fruit than copper compounds. However, *Erwinia amylovora* has developed resistance to streptomycin in many states where it has been used, including California, Oregon, Washington, Missouri, and Michigan. Further, an antibiotic program is expensive and many countries in Europe prohibit its use.

Biological control of fire blight has also been attempted. Such efforts have been particularly directed to developing organisms antagonistic to *Erwinia amylovora*. Biological control studies indicate that such techniques have potential usefulness in controlling fire blight, but none of the tested procedures are sufficiently effective or developed to replace chemical treatments.

In view of the deficiencies of present techniques of combating fire blight in pomaceous fruit, the need remains for an effective treatment procedure.

SUMMARY OF THE INVENTION

The present invention relates to a method of conferring resistance against fire blight to pomaceous fruit scion or rootstock cultivars. In accordance with the invention, pomaceous fruit scion or rootstock cultivars are transformed with a gene which encodes for a lytic protein. Such transformation can be carried out by contacting tissue of the cultivar with an inoculum of bacterium of the genus Agrobacterium which is transformed with a vector comprising the gene encoding for a lytic protein. Alternatively, transformation of the cultivar can be carried out by propelling inert or biologically active particles at cultivar tissue. This causes the vector comprising a gene encoding for a lytic protein, which is either associated with the particles or around cells of the tissue, to be introduced into the interior of the cells. Once transformed, the cultivars are regenerated to form a transgenic pomaceous fruit tree. It is particularly desirable to utilize the present invention in conjunction with apple and pear trees. A wide variety of rootstock and scion cultivars for each can be utilized.

Also encompassed by the present invention is a transgenic pomaceous fruit, particularly apple or pear, scion or rootstock cultivar transformed with a gene which encodes for a lytic protein. In addition, a transgenic pomaceous fruit tree transformed with that gene is also disclosed. Incorporation of that gene imparts fire blight resistance.

Fire blight resistant transgenic variants of the current commercial fruiting cultivars (scions) and rootstocks of apples and pears allows for more complete control of fire blight while retaining the varietal characteristics of specific cultivars. Such fire blight control is possible without environmental and food contamination, resulting from use of chemicals and antibiotics. The interests of the public health, the environment, and the economics of fruit growing are all benefited by the present invention.

BRIEF DESCRIPTION OF THE DRAWINGS

FIG. 1 shows the nucleotide (SEQ. ID. No. 3) and the amino acid (SEQ. ID. No. 4) for chicken (egg white) lysozyme and a restriction map of that insert in plasmid vector plys1023.

FIG. 12 is a schematic drawing showing the steps of forming plasmid vector pLDB14.

FIG. 13 shows the nucleotide (SEQ ID No. 9) and amino acid (SEQ ID No. 10) sequences of the cDNA sequence for mature Attacin E (564 base pairs) together with a 3' non-coding region (159 base pairs) and a restriction map of the insert in the attacin clone pCP521.

DETAILED DESCRIPTION OF THE INVENTION AND DRAWINGS

Figure 2:
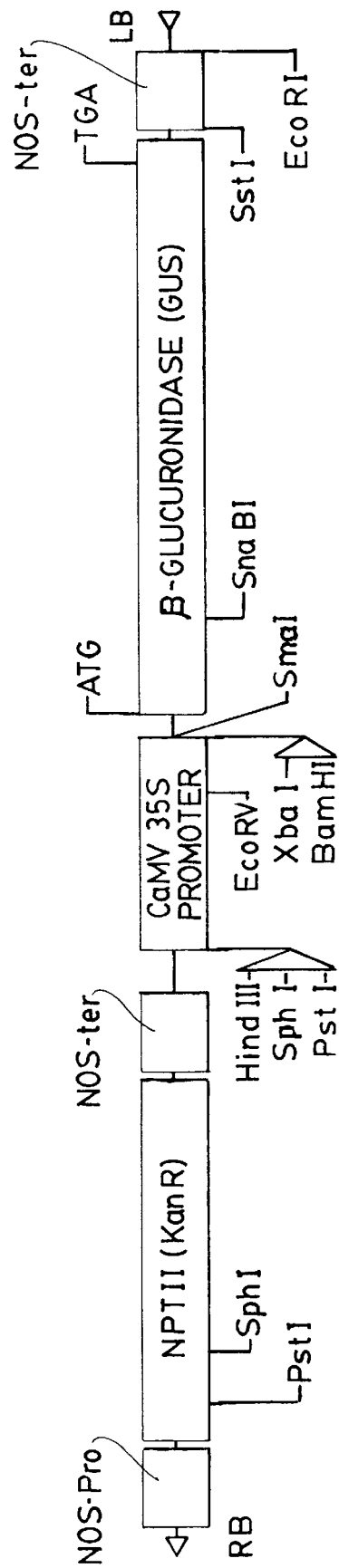
FIG. 2 is a map of the transfer DNA ("T-DNA") of plasmid vector pBI121.

The present invention relates to a method of conferring resistance against fire blight to pomaceous fruit scion or rootstock cultivars and to pomaceous fruit scion and rootstock cultivars per se having such resistance. The process of conferring fire blight resistance includes transforming pomaceous fruit scion or rootstock cultivars with a gene which encodes a lytic protein. Once transformation has occurred, the cultivar is regenerated to form a transgenic pomaceous fruit tree.

Plant tissues suitable for transformation include leaf tissue, root tissue, meristems, and protoplasts. It is particularly preferred to utilize leaf tissue.

One technique of transforming pomaceous fruit scion or rootstock cultivars with a gene which encodes for a lytic protein is by contacting the tissue of such a cultivar with an inoculum of a bacteria transformed with a vector comprising a gene that encodes for a lytic protein. Generally, this procedure involves inoculating the apple or pear tissue with a suspension of bacteria and incubating the tissue for 48 to 72 hours on regeneration medium without antibiotics at 25°–28° C.

Bacteria from the genus Agrobacterium can be utilized to transform plant cells. Suitable species of such bacterium include *Agrobacterium tumefaciens* and *Agrobacterium rhizogenes*. *Agrobacterium tumefaciens* (e.g., strains LBA4404 or EHA105) is particularly useful due to its well-known ability to transform plants.

In inoculating the tissue of pomaceous fruit scion or rootstock cultivars with Agrobacterium, the bacteria must be transformed with a vector which includes a gene encoding for a lytic protein. Suitable proteins include lysozyme, attacins, cecropins, and homologs thereof. It is known that various pupae of silk moths can be immunized with non-pathogenic bacteria or heat-killed pathogens to produce a set of such proteins which are not normally present in the hemolymph of these animals. Although the injection of such bacteria or pathogens has been carried out with a number of different insects, diapausing pupae of the giant silk moth *Hyalophora cecropia* have proven particularly effective. Several of the proteins produced by such immunized moths have been found to have lytic activity (i.e. causing cells to lyse) against a broad range of gram-negative and gram-positive bacteria.

Lysozyme is one suitable lytic peptide. It limits the growth of a broad spectrum of bacteria. As set forth in J. M. Jaynes, et al., "Increasing Bacterial Resistance in Plants Utilizing Antibacterial Genes from Insects," *BioEssays* 6:263–270 (1987), which is hereby incorporated by reference, the nucleotide (SEQ. ID. No. 1) and amino acid (SEQ. ID. No. 2) sequences of lysozyme from *Hyalophora cecropia*, are as follows:

| TGC | CGT | TCG | CAG | TTC | GCT | TTG | CAT | TGC | GAT | GCG | AAA | CGT | TTC | ACG | AGA | TGC | GGG |
|---|---|---|---|---|---|---|---|---|---|---|---|---|---|---|---|---|---|
| Cys | Arg | Ser | Gln | Phe | Ala | Leu | His | Cys | Asp | Ala | Lys | Arg | Phe | Thr | Arg | Cys | Gly |

| TTA | GTG | CAG | GAG | CTT | AGG | AGA | CGA | GGC | TTC | GAT | GAA | ACT | TTG | ATG | AGT | AAC | TGG |
|---|---|---|---|---|---|---|---|---|---|---|---|---|---|---|---|---|---|
| Leu | Val | Gln | Glu | Leu | Arg | Arg | Arg | Gly | Phe | Asp | Glu | Thr | Leu | Met | Ser | Asn | Trp |

-continued

| GTC | TGC | CTT | GTC | GAG | AAC | GAA | AGC | GGA | CGG | TTT | ACC | GAT | AAA | ATC | GGT | AAA | GTT |
|-----|-----|-----|-----|-----|-----|-----|-----|-----|-----|-----|-----|-----|-----|-----|-----|-----|-----|
| Val | Cys | Leu | Val | Glu | Asn | Glu | Ser | Gly | Arg | Phe | Thr | Asp | Lys | Ile | Gly | Lys | Val |
| AAC | AAG | AAC | GGA | TCT | CGA | GAC | TAC | GGC | CTC | TTC | CAG | ATC | AAT | GAC | AAA | TAC | TGG |
| Asn | Lys | Asn | Gly | Ser | Arg | Asp | Tyr | Gly | Leu | Phe | Gln | Ile | Asn | Asp | Lys | Tyr | Trp |
| TGC | AGT | AAG | GGA | TCC | ACT | CCT | GGA | AAG | GAT | TGC | AAC | GTG | ACT | TGT | AAT | CAG | CTA |
| Cys | Ser | Lys | Gly | Ser | Thr | Pro | Gly | Lys | Asp | Cys | Asn | Val | Thr | Cys | Asn | Gln | Leu |
| CTG | ACT | GAC | GAC | ATT | AGC | GTG | GCA | GCT | ACG | TGC | GCG | AAG | AAG | ATT | TAC | AAA | CGC |
| Leu | Thr | Asp | Asp | Ile | Ser | Val | Ala | Ala | Thr | Cys | Ala | Lys | Lys | Ile | Tyr | Lys | Arg |
| CAC | AAG | TTT | GAC | GCT | TGG | TAC | GGA | TGG | AAA | AAT | CAC | TGT | CAA | CAT | GGA | CTG | CCA |
| His | Lys | Phe | Asp | Ala | Trp | Tyr | Gly | Trp | Lys | Asn | His | Cys | Gln | His | Gly | Leu | Pro |
| GAT | ATT | AGC | GAC | TGT | TAG | | | | | | | | | | | | |
| Asp | Ile | Ser | Asp | Cys | Stop | | | | | | | | | | | | |

The nucleotides and amino acid sequences in bold face, respectively, encode for or constitute a partial leader peptide. The nucleotide (SEQ. ID. No. 3) and amino acid (SEQ. ID. No. 4) for chicken (egg white) lysozyme and a restriction map of that insert in the plasmid vector plys1023 is shown in FIG. 1. The cloning of these sequences into plasmid vectors is set forth in L. Destefano Beltran, "The Introduction into Tobacco Plants of Genes which Encode Some of the Natural Components of the Humoral Immune Response of *Hyalaphora cecropia*, A. Dissertation Submitted to Loui-siana State University" (1991) ("Destafano Beltran Thesis"), which is hereby incorporated by reference. Variations of these nucleotide/amino acid sequences are also known.

Another group of lytic proteins which has been found to have an antibacterial activity in immunized *Hyalophora cecropia* are attacins. Attacins are the largest lytic proteins from this source with a molecular weight of about 20,000 daltons. There are six slightly different forms of attacins— i.e. Attacins A through F. Two genes are responsible for producing the attacins with the 6 specific attacins resulting from post-translational modification. Attacin E is a neutral-acidic form of attacin that results from the non-modified translation of one of the two attacin genes. Tests using the amino acid sequence of the N-terminus of five of the attacins indicate the presence of 3 basic and 2 acidic forms which differ slightly from each other. The deduced nucleotide (SEQ. ID. No. 5) and amino acid (SEQ. ID. No. 6) sequences for Attacin E are disclosed in J. M. Jaynes, et al., "Increasing Bacterial Resistance in Plants Utilizing Antibacterial Genes from Insects," *BioEssays* 6:263–270 (1987), which is hereby incorporated by reference, as follows:

| GAC | GCG | CAC | GGA | GCC | CTT | ACG | CTC | AAC | TCC | GAT | GGT | ACC | TCT | GGT | GCT | GTG | GTT |
|-----|-----|-----|-----|-----|-----|-----|-----|-----|-----|-----|-----|-----|-----|-----|-----|-----|-----|
| Asp | Ala | His | Gly | Ala | Leu | Thr | Leu | Asn | Ser | Asp | Gly | Thr | Ser | Gly | Ala | Val | Val |
| AAA | GTA | CCC | TTT | GCT | GGT | AAC | GAC | AAG | AAT | ATA | GTA | AGC | GCT | ATC | GGT | TCC | GTA |
| Lys | Val | Pro | Phe | Ala | Gly | Asn | Asp | Lys | Asn | Ile | Val | Ser | Ala | Ile | Gly | Ser | Val |
| GAC | TTA | ACT | GAT | AGG | CAG | AAA | CTA | GGC | GCT | GCA | ACC | GCT | GGA | GTG | GCA | CTG | GAT |
| Asp | Leu | Thr | Asp | Arg | Gln | Lys | Leu | Gly | Ala | Ala | Thr | Ala | Gly | Val | Ala | Leu | Asp |
| AAT | ATA | AAC | GGT | CAC | GGA | CTA | AGT | CTC | ACG | GAT | ACA | CAC | ATC | CCC | GGG | TTC | GGA |
| Asn | Ile | Asn | Gly | His | Gly | Leu | Ser | Leu | Thr | Asp | Thr | His | Ile | Pro | Gly | Phe | Gly |
| GAC | AAG | ATG | ACA | GCA | GCC | GGC | AAA | GTG | AAT | GTC | TTC | CAC | AAT | GAT | AAC | CAC | GAC |
| Asp | Lys | Met | Thr | Ala | Ala | Gly | Lys | Val | Asn | Val | Phe | His | Asn | Asp | Asn | His | Asp |
| ATC | ACA | GCG | AAG | GCT | TTC | GCC | ACC | AGA | AAC | ATG | CCG | GAT | ATT | GCT | AAT | GTA | CCT |
| Ile | Thr | Ala | Lys | Ala | Phe | Ala | Thr | Arg | Asn | Met | Pro | Asp | Ile | Ala | Asn | Val | Pro |
| AAT | TTC | AAC | ACT | GTC | GGT | GGC | GGA | ATA | GAC | TAT | ATG | TTC | AAA | GAT | AAG | ATT | GGT |
| Asn | Phe | Asn | Thr | Val | Gly | Gly | Gly | Ile | Asp | Tyr | Met | Phe | Lys | Asp | Lys | Ile | Gly |
| GCA | TCT | GCG | AGC | GCC | GCT | CAC | ACG | GAC | TTT | ATC | AAT | CGC | AAC | GAC | TAC | TCT | CTT |
| Ala | Ser | Ala | Ser | Ala | Ala | His | Thr | Asp | Phe | Ile | Asn | Arg | Asn | Asp | Tyr | Ser | Leu |
| GAC | GGG | AAA | CTG | AAC | CTC | TTC | AAG | ACT | CCT | GAT | ACC | TCG | ATT | GAT | TTC | AAC | GCC |
| Asp | Gly | Lys | Leu | Asn | Leu | Phe | Lys | Thr | Pro | Asp | Thr | Ser | Ile | Asp | Phe | Asn | Ala |
| GGT | TTC | AAG | AAG | TTC | GAT | ACA | CCT | TTC | ATG | AAG | TCC | TCT | TGG | GAG | CCT | AAC | TTC |
| Gly | Phe | Lys | Lys | Phe | Asp | Thr | Pro | Phe | Met | Lys | Ser | Ser | Trp | Glu | Pro | Asn | Phe |
| GGA | TTC | TCA | CTT | TCT | AAA | TAT | TTC | TGA | | | | | | | | | |
| Gly | Phe | Ser | Leu | Ser | Lys | Tyr | Phe | Stop | | | | | | | | | |

The cDNA nucleotide and amino acid sequences for the other attacins are disclosed in A. Engstrom et al., "Insect Immunity. The Primary Structure of the Antibacterial Protein Attacin F and its Relation to the Two Native Attacins from *Hyalophora cecropin*", *EMBO J.*, vol. 3, no. 9, pp. 2065–70 (1984) and K. Kockum, et. al., "Insect Immunity. Isolation and Sequence of two cDNA Clones Corresponding to Acidic and Basic Attacins from *Hyalophora cecropra*", *EMBO J.*, vol. 3, no. 9, pp. 2071–75 (1984), which are hereby incorporated by reference.

Cecropins are the most potent antibacterial peptide with a broad spectrum of activity against both gram-negative and gram-positive bacteria. They are small and found in three major forms—i.e. Cecropin A, Cecropin B, and Cecropin D. They all have a high degree of homology with a basic N-terminal region and a hydrophobic stretch in the C-terminal part of the molecule. The amino acid (SEQ. ID. No. 7) sequence for Cecropin A is disclosed in WO 89/04371, which is hereby incorporated by reference, as follows:

Lys Trp Lys Leu Phe Lys Lys Ile Glu Lys Val Gly Gln Asn Ile Arg

Asp Gly Ile Ile Lys Ala Gly Pro Ala Val Ala Val Val Gly Gln Ala

Thr Gln Ile Ala Lys

From this amino acid sequence, suitable nucleotide sequences can be derived by those skilled in the art. The nucleotide (SEQ. ID. No. 8) and amino acid (SEQ. ID. No. 9) sequences of the clone encoding for the precursor of Cecropin B is disclosed in J. M. Jaynes, et al., "Increasing Bacterial Resistance in Plants Utilizing Antibacterial Genes from Insects," *BioEssays* 6:263–270 (1987), which is incorporated by reference, as follows:

| | | | | | | | | | | | | | | | |
|---|---|---|---|---|---|---|---|---|---|---|---|---|---|---|---|
| ATG | AAT | TTC | TCA | AGG | ATA | TTT | TTC | TTC | GTG | TTC | GCT | TTG | GTT | CTG | GCT |
| Met | Asn | Phe | Ser | Arg | Ile | Phe | Phe | Phe | Val | Phe | Ala | Leu | Val | Leu | Ala |

| TCA | ACA | GTT | TCG | GCT | GCA | CCG | GAG | CCG | AAA | TGG | AAA | GTC | TTC | AAG | AAA |
| Ser | Thr | Val | Ser | Ala | Ala | Pro | Glu | Pro | Lys | Trp | Lys | Val | Phe | Lys | Lys |

| ATT | GAA | AAA | ATG | GGT | CGC | AAC | ATT | CGA | AAC | CGT | ATT | GTC | AAG | GCT | GGA |
| Ile | Glu | Lys | Met | Gly | Arg | Asn | Ile | Arg | Asn | Gly | Ile | Val | Lys | Ala | Gly |
| CCA | GCG | ATC | GCG | GTT | TTA | GGC | GAA | GCC | AAA | GCG | CTA | GGA | TAA | | |
| Pro | Ala | Ile | Ala | Val | Leu | Gly | Glu | Ala | Lys | Ala | Leu | Gly | Stop | | |

The nucleotide and amino acid sequences in bold face, respectively, encode for or constitute a leader peptide. The amino acid sequence (SEQ. ID. No. 10) for Cecropin D is disclosed in WO 89/04371, which is hereby incorporated by reference, as follows:

Trp Asn Pro Phe Lys Glu Leu Glu Lys Val Gly Gln Arg Val Arg Asp
Ala Val Ile Ser Ala Gly Pro Ala Val Ala Thr Val Ala Asn Ala Thr
Ala Leu Ala Lys

From this amino acid sequence, suitable nucleotide sequences can be derived by those skilled in the art.

Synthetic homologs of lysozyme, attacins, and cecropins have also been developed. One example of such a synthetic peptide is Shiva I which was designed with highly significant differences in sequence homology while maintaining charge distribution, amphipathy, and hydrophobic properties of natural cecropin B. Its amino acid sequence (SEQ. ID. No. 11) is described in L. Destéfano-Beltrán, et al., "Enhancing Bacterial and Fungal Disease Resistance in Plants: Application to Potato," *The Molecular and Cellular Biology of the Potato*, Vayda M. E. and Park W. D. (eds), CAB International Wallingford, UK pp. 205–221 (1990), which is hereby incorporated by reference, as follows:

Met Pro Arg Trp Arg Leu Phe Arg Arg Ile Asp Arg Val Gly Lys Gln
Ile Lys Gln Ile Leu Arg Ala Gly Pro Ala Ile Ala Leu Val Gly Asp
Ala Arg Ala Val Gly

From this amino acid sequence, suitable nucleotide sequences can be derived by those skilled in the art.

Another known homolog is the synthetic peptide SB-37 which has minor changes from the parent cecropin B molecule due to substitution of methionine 11 with valine and addition of an $NH_2$-terminal methionine, proline. The amino acid sequence (SEQ. ID. No. 12) for this peptide is disclosed in L. Destéfano-Beltrán, et al., "Enhancing Bacterial and Fungal Disease Resistance in Plants: Application to Potato," Vayda M. E. and Park W. D. (eds), CAB International Walling Ford, UK pp. 203–221 (1990), which is hereby incorporated by reference, as follows:

Met Pro Lys Trp Lys Val Phe Lys Lys Ile Glu Lys Val Gly Arg Asn
Ile Arg Asn Gly Ile Val Lys Ala Gly Pro Ala Ile Ala Val Leu Gly
Glu Ala Lys Ala Leu Gly

From this amino acid sequence, suitable nucleotide sequences can be derived by those skilled in the art.

To permit export of lytic proteins from plant cells, the gene coding for that protein is fused to a gene coding for a signal peptide. As a result, a fusion protein containing the signal peptide joined to the lytic protein is formed. The presence of the signal peptide directs the fusion protein to the cell's endoplasmic reticulum where the signal sequence is cleaved. The lytic protein is then modified in the endoplasmic reticulum lumen or in the Golgi complex and secreted outside the cell.

It is possible to utilize this concept in conjunction with any of the lytic proteins identified above. Particularly useful fusion proteins are sPR1 or sCEC signal peptides fused to Shiva I or SB-37 (i.e. sPR1-Shiva I, sPR1-SB37, sCEC-Shiva I, and sCEC-CSB37). See J. Denecke, "Protein Secretion in Plant Cells Can Occur via a Default Pathway," *The Plant Cell*, vol. 2, pp. 51–59 (1990), which is hereby incorporated by reference.

The nucleotide (SEQ. ID. No. 13) and amino acid (SEQ. ID. No. 14) sequences for sCEC-Shiva I are as follows:

| | | | | | | | | | | | | | | | |
|---|---|---|---|---|---|---|---|---|---|---|---|---|---|---|---|
| ATG | AAC | TTT | TCT | AGG | ATC | TTC | TTT | TTC | GTG | TTC | GCT | CTT | GTT | CTC | GCC |
| Met | Asn | Phe | Ser | Arg | Ile | Phe | Phe | Phe | Val | Phe | Ala | Leu | Val | Leu | Ala |

| TTG | TCC | ACT | GTG | TCT | GCC | GCT | CCT | GAC | ATG | CCG | CGC | TGG | CGT | CTG | TTC |
| Leu | Ser | Thr | Val | Ser | Ala | Ala | Pro | Asp | Met | Pro | Arg | Trp | Arg | Leu | Phe |

| CGC | CGT | ATC | GAC | CGT | GTT | GGC | AAA | CAG | ATC | AAA | CAG | GGT | ATC | CTG | CGT |
| Arg | Arg | Ile | Asp | Arg | Val | Gly | Lys | Gln | Ile | Lys | Gln | Gly | Ile | Leu | Arg |
| GCT | GGC | CCG | GCT | ATC | GCT | CTG | GTT | GGC | GAC | GCC | CGC | GCA | GTT | GGT | |
| Ala | Gly | Pro | Ala | Ile | Ala | Leu | Val | Gly | Asp | Ala | Arg | Ala | Val | Gly | |

TGA GAA TTC GCT AGC AAG CTT
Stop

The nucleotide and amino acid sequences in bold face respectively, encode for or constitute the signal peptide.

The nucleotide (SEQ. ID. No. 15) and amino acid (SEQ. ID. No. 16) sequences for sCEC-SB37 are as follows:

ATG AAC TTT TCT AGG ATC TTC TTT TTC GTG TTC GCT CTT GTT CTC GCC
Met Asn Phe Ser Arg Ile Phe Phe Phe Val Phe Ala Leu Val Leu Ala

TTG TCC ACT GTG TCT GCC GCT CCT GAG CCG AAA TGG AAA GTC TTC AAG
Leu Ser Thr Val Ser Ala Ala Pro Glu Pro Lys Trp Lys Val Phe Lys

AAA ATT GAA AAA GTC GGT CGC AAC ATT CGA AAC GGT ATT GTC AAG GCT
Lys Ile Glu Lys Val Gly Arg Asn Ile Arg Asn Gly Ile Val Lys Ala

GGA CCA GCG ATC GCG GTT TTA GGC GAA GCC AAA GCG CTA GGA TAA GAA
Gly Pro Ala Ile Ala Val Leu Gly Glu Ala Lys Ala Leu Gly Stop

TTC GCT AGC AAG CTT

Again, the nucleotide and amino acid sequences in bold face respectively, encode for or constitute the signal peptide.

The nucleotide (SEQ. ID. No. 17) and amino acid (SEQ. ID. No. 18) sequences for sPR1-Shiva I are as follows:

ATG GGA TTT TTC CTT TTT TCT CAA ATG CCA TCC TTC TTT CTC GTG TCC
Met Gly Phe Phe Leu Phe Ser Glu Met Pro Ser Phe Phe Leu Val Ser

ACT CTT CTC CTT TTC CTC ATT ATC TCT CAC TCC TCT CAT GCT ACC ATG
Thr Leu Leu Leu Phe Leu Ile Ile Ser His Ser Ser Ala Ala Thr Met

CCG CGC TGG CGT CTG TTC CGC CGT ATC GAC CGT GTT GGC AAA
Pro Arg Trp Arg Leu Phe Arg Arg Ile Asp Arg Val Gly Lys

CAG ATC AAA CAG GGT ATC CTG CGT GCT AGC CCG GCT ATC GCT GCT CGT GTT
Gln Ile Lys Gln Gly Ile Leu Arg Ala Gly Pro Ala Ile Ala Ala Leu Val

GGC GAC GCC CGC GCA GTT GGT TGA GAA TTC
Gly Asp Ala Arg Ala Val Gly STOP

The nucleotide and amino acid sequences in bold face respectively encode for or constitute the signal peptide.

The nucleotide (SEQ. ID. No. 19) and amino acid (SEQ. ID. No. 20) for sPR1-SB37 are as follows:

ATG GGA TTT TTC CTT TTT TCT CAA ATG CCA TCC TTC TTT CTC GTG TCC
Met Gly Phe Phe Leu Phe Ser Glu Met Pro Ser Phe Phe Leu Val Ser

ACT CTT CTC CTT TTC CTC ATT ATC TCT CAC TCC TCT CAT GCT ATG CCG
Thr Leu Leu Leu Phe Leu Ile Ile Ser His Ser Ser Ala Ala Met Pro

AAA TGG AAA GTC TTC AAG AAA ATT GAA AAA GTC GGT CGC AAC ATT CGA
Lys Try Lys Val Phe Lys Lys Ile Glu Lys Val Gly Arg Asn Ile Arg

AAC GGT ATT GTC AAG GCT GGA CCA GCG ATC GCG GTT TTA GGC GAA GCC
Asn Gly Ile Val Lys Ala Gly Pro Ala Ile Ala Val Leu Gly Glu Ala

AAA GCG CTA GGA TAA GAA TTC
Lys Ala Leu Gly STOP

The nucleotide and amino acid sequences in bold face, respectively encode for or constitute the signal peptide.

Other lytic proteins which may be suitable include metittins, magainins, bombinins, xenopsins, caeruleins, and sarcotoxins. The amino acid sequences for these and other useful lytic proteins are disclosed in WO 89/04371, which is hereby incorporated by reference, particularly Table I therein.

Figure 3:
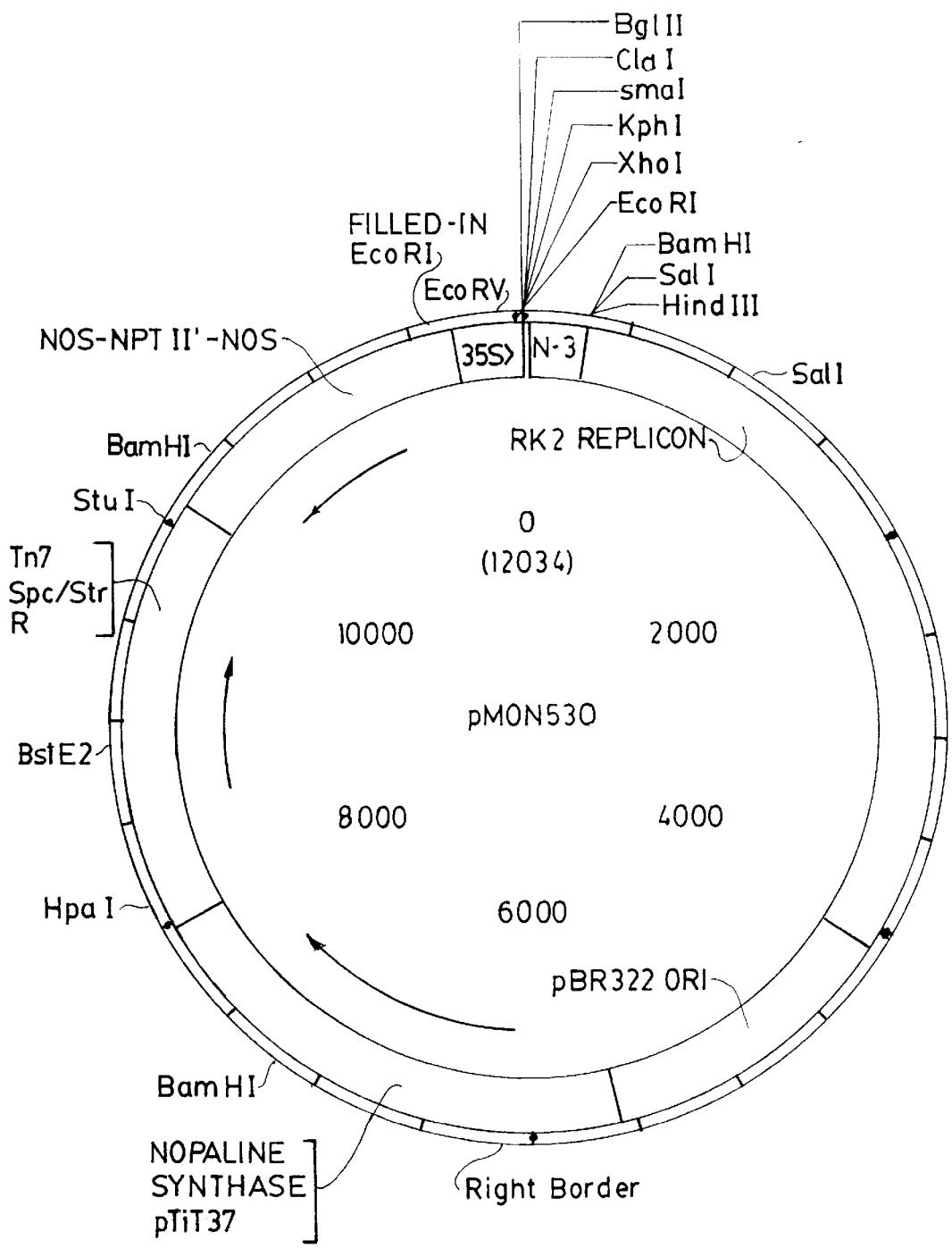
FIG. 3 is a map of plasmid vector pMON530.
Figure 4:
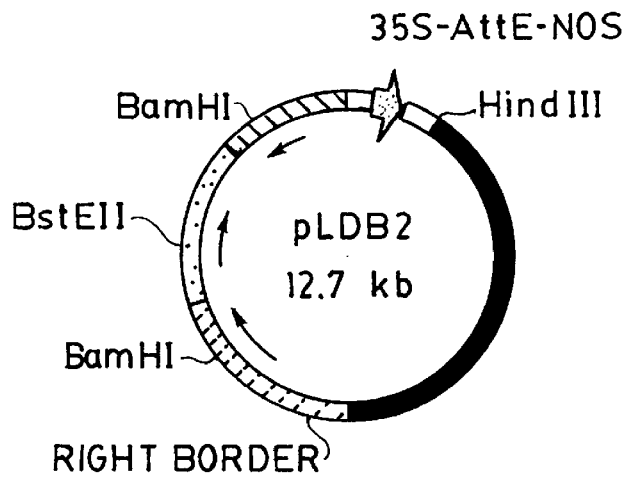
FIG. 4 is a map of plasmid vector pLDB2.
Figure 5:
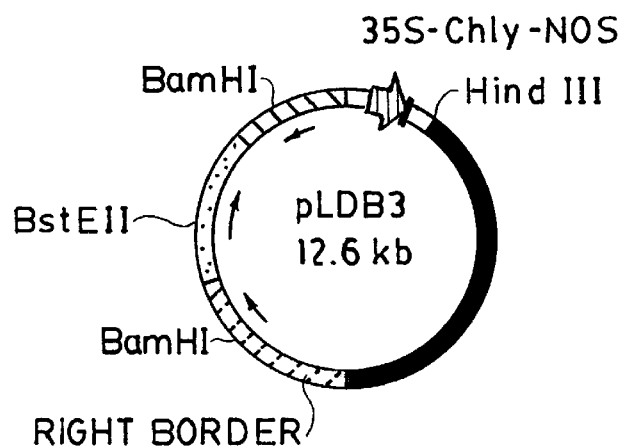
FIG. 5 is a map of plasmid vector pLDB3.
Figure 6:
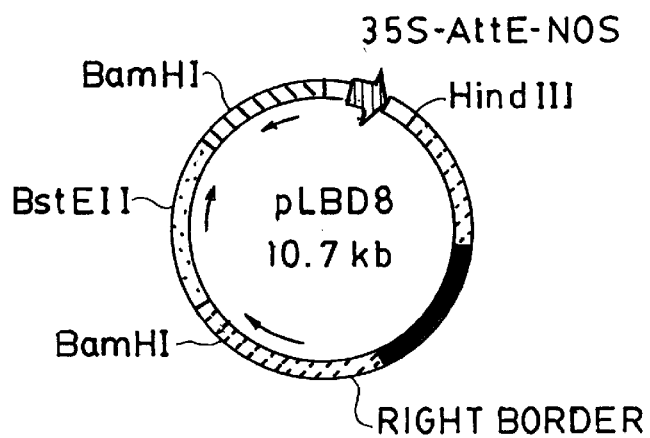
FIG. 6 is a map of plasmid vector pLDB8.
Figure 7:
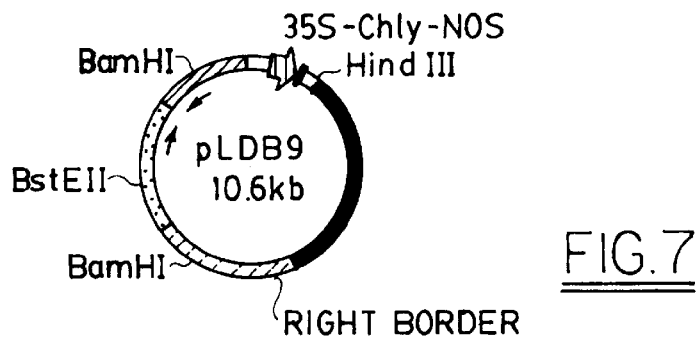
FIG. 7 is a map of plasmid vector pLDB9.
Figure 8:
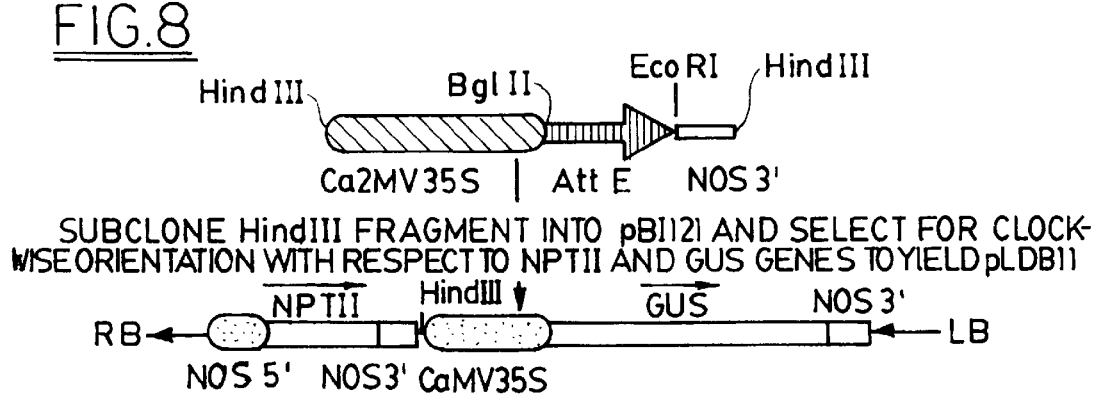
FIG. 8 is a map of T-DNA of plasmid vector pLDB11.
Figure 9:
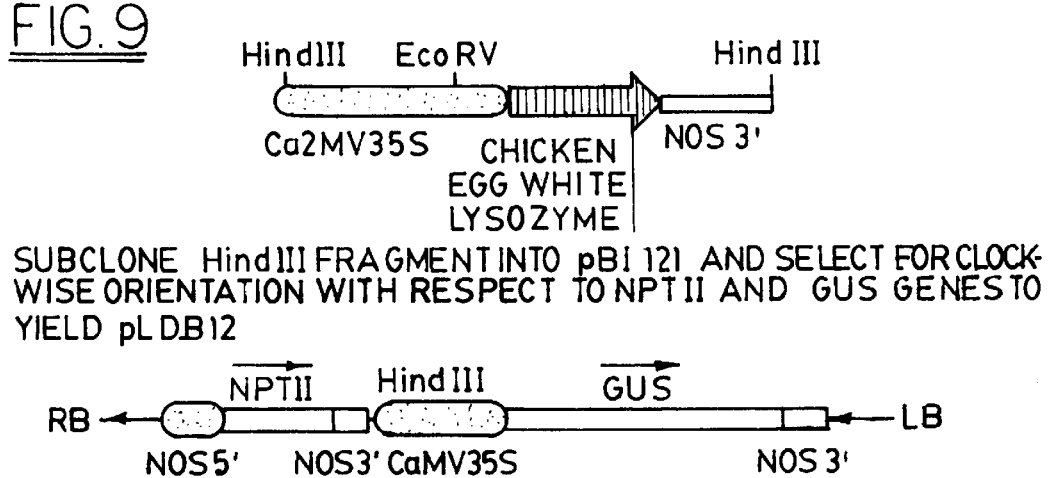
FIG. 9 is a map of T-DNA of plasmid vector pLDB12.

Vectors, suitable for incorporation in Agrobacterium, which include a gene encoding for a lytic protein, can be in the form of plasmids. Such plasmids contain an origin of replication for replication in the bacterium *Escherichia coli*, an origin of replication for replication in the bacterium *Agrobacterium tumefaciens*, T-DNA right border sequences for transfer of genes to plants, and marker genes for selection of transformed plant cells. Particularly preferred is the vector pBI121 which contains a low-copy RK2 origin of replication, the neomycin phosphotransferase (nptII) marker gene with a nopaline synthase (NOS) promoter and a NOS 3' polyadenylation signal, and the β-glucuronidase (GUS)

marker gene with a CaMV 35S promoter and a NOS 3' polyadenylation signal. FIG. 2 is a map of T-DNA plasmid vector pBI121, which is available from Clonetech Laboratories, Inc., 4030 Fabian Way, Palo Alto, Calif. 94303. Other suitable vectors include pMON530 (FIG. 3) and pMON200 (see FIG. 10). A gene encoding for a lytic protein is inserted into the vector. For lytic protein production, the following plasmids are useful: pLDB15 (see FIG. 15) which encodes Attacin E protein; pLDB1 (see FIG. 10) which encodes for SB-37 lytic peptide; pLDB2 (see FIG. 4) which encodes Attacin E protein, pLDB3 (see FIG. 5) which encodes chicken lysozyme; pLDB4 which encodes T4 phage lysozyme; pLDB5 which encodes P22 protein gene 13; pLDB6 which encodes P22 lysozyme gene 19; pLDB7 (see FIG. 10) which encodes SB-37 lytic protein; pLDB8 (see FIG. 6) which encodes Attacin E protein; pLDB9 (see FIG. 7) which encodes chicken lysozyme; pLDB10 (see FIG. 11) which encodes SB-37 lytic peptide; pLDB11 (see FIG. 8) which encodes Attacin E protein; pLDB12 (see FIG. 9) which encodes chicken lysozyme; pLDB14 (see FIG. 12) which encodes SB-37 lytic peptide; pLDB16 which encodes T4 phage lysozyme; pLDB18 which encodes genomic cecropin B; pWIShiva-1 which encodes Shiva-1 lytic peptide; pWIP19 which encodes P22 lysozyme gene 19; and pCa2P19 which encodes P22 lysozyme gene 19. The characteristics of these plasmids are set forth below in Table I.

TABLE I

| Construct | Gene Cloned | Vector | Promoter |
|---|---|---|---|
| pLDB1 | SB-37 Lytic Peptide | pMON530 | CAMV 35S |
| pLDB2 | Attacin Lysozyme | PMON530 | CAMV 35S |
| pLDB3 | Chicken Lysozyme | pMON530 | CAMV 35S |
| pLDB4 | T4 Phage Lysozyme | pMON530 | CAMV 35S |
| pLDB5 | P22 Protein gene 13 | pMON530 | CAMV 35S |
| pLDB6 | P22 Lysozyme gene 19 | pMON530 | CAMV 35S |
| pLDB7 | SB-37 Lytic Peptide | PMON316 | CAMV 35S |
| pLDB8 | Attacin E Protein | PMON316 | CAMV 35S |
| pLDB9 | Chicken Lysozyme | pMON316 | CAMV 35S |
| pLDB10 | SB-37 Lytic Peptide | pBI121 | Double 35S |
| pLDB11 | Attacin E Protein | PBI121 | Double 35S |
| pLDB12 | Chicken Lysozyme | pBI121 | Double 35S |
| pLDB14 | SB-37 Lytic Peptide | PBI121 | Proteinase Inh. II |
| pLDB15 | Attacin E Protein | pBI121 | Proteinase Inh. II |
| pLDB16 | T4 Phage Lysozyme | pBI121 | Double 35S |
| pLDB17 | P22 Protein gene 13 | pBI121 | Double 35S |
| pLDB18 | Genomic Cecropin B | pMON200 | Cecropin B |
| pWIShiva-1 | Shiva-1 Lytic Peptide | pBI121 | Proteinase Inh. II |
| pWIP19 | P22 Lysozyme gene 19 | pBI121 | Proteinase Inh. II |
| pCa2P19 | P22 Lysozyme gene 19 | pBI121 | Double 35S |

Figure 20:
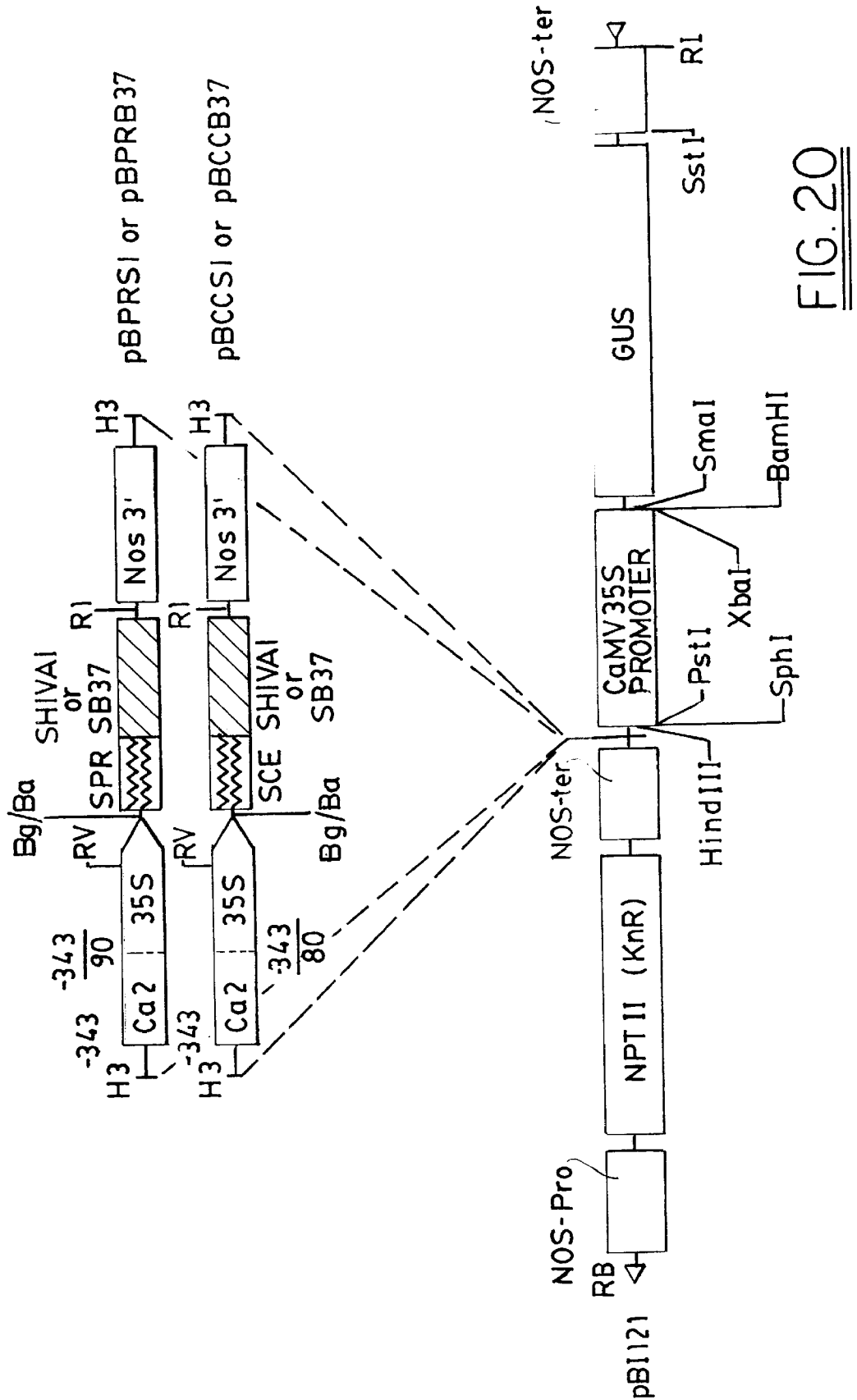
FIG. 20 are maps of T-DNA of plasmid vectors pBPRS1, pBPRB37, pBCCS, and pBCCB37.

From Table I and the examples which follow preparation of the plasmid vectors in Table I would be apparent to one of ordinary skill in the art, particularly in view of the Destéfano Beltrán Thesis, which is hereby incorporated by reference. All these plasmids are disclosed in L. Destéfano-Beltrán, "Enhancing Bacterial and Fungal Disease Resistance in Plants: Application to Potato," *The Molecular and Cellular Biology of the Potato*, Vayda M. E. and Park W. D. (eds), CAB International, Wallingford, UK pp. 205–221 (1990), which is hereby incorporated by reference. In addition, the following plasmids are also useful for production of lytic peptides: pBPRS1 which encodes for the sPR1-Shiva-1 fusion protein, pBCCS1 which encodes for the sCEC-Shiva-1 fusion protein, pBPRB37 which encodes for the sPR1-SB37 fusion protein, and pBCCB37 which encodes for the sCEC-SB37 fusion protein. See FIG. 20. Typically, Agrobacterium spp. are transformed with plasmid vectors by direct uptake of plasmid DNA after chemical and heat treatment, as described by M. Holsters et al., "Transfection and Transformation of *Agrobacterium tumefaciens*." *Mol Gen Genet* 163:181–187 (1978); by direct uptake of plasmid DNA after electroporation, as described by S. Wen-jun and B. Forde, "Efficient Transformation of *Agrobacterium spp*. by High Voltage Electroporation," *Nucleic Acids Res* 17:8385 (1989); by triparental conjugational transfer of plasmids from *Escherichia coli* to Agrobacterium mediated by a Tra+helper strain as described by G. Ditta et al., "Broad Host Range DNA Cloning System for Gram-negative Bacteria: Construction of a Gene Bank of *Rhizobium meliloti*," *Proc Natl Acad Sci USA* 77:7347–7351 (1981); or by direct conjugational transfer from *Escherichia coli* to Agrobacterium as described by R. Simon et al., "A Broad Host Range Mobilization System for in vivo Genetic Engineering: Transposon Mutagenesis in Gram-negative Bacteria," *Biotechnology* 1:784–791 (1982). All of these publications are hereby incorporated by reference.

Another approach to transforming pomaceous fruit scion or rootstock cultivars with a gene which encodes for a lytic protein is by propelling inert or biologically active particles at cultivar tissues cells. This technique is disclosed in U.S. Pat. Nos. 4,945,050, 5,036,006, and 5,100,792 all to Sanford et al., which are hereby incorporated by reference. Generally, this procedure involves propelling inert or biologically active particles at the cells of cultivar tissues under conditions effective to penetrate the outer surface of the cell and to be incorporated within the interior thereof. When inert particles are utilized, the vector can be introduced into the cell by coating the particles with the vector encoding the gene for a lytic protein. Alternatively, the target cell can be surrounded by the vector so that the vector is carried into the cell by the wake of the particle. Biologically active particles (e.g., dried bacterium or a bacteriophage, each containing DNA sought to be introduced) can also be propelled into cultivar cell tissue.

Once a pomaceous fruit scion or rootstock cultivar is transformed in accordance with the present invention, it is regenerated to form a transgenic pomaceous fruit tree. Generally, regeneration is accomplished by culturing transformed tissue on medium containing the appropriate growth regulators and nutrients to allow for the initiation of shoot meristems. Appropriate antibiotics are added to the regeneration medium to inhibit the growth of Agrobacterium and to select for the development of transformed cells. Following shoot initiation, shoots are allowed to develop in tissue culture and are screened for marker gene activity.

The technique of imparting fire blight resistance to pomaceous fruit is useful in conjunction with any member of the Rosaceae family. Of these, apples, pears, and quince are particularly prominent. Other species of the Rosaceae family to which fire blight resistance can be imparted, pursuant to the present invention, include cotoneaster, crataegus, cydonia, pyracantha, and sorbus.

For apples, the following cultivars can be treated in accordance with present invention to impart fire blight resistance: Adina, Akane, Anna, Antonovka, Arkansas Black, Bancroft, Beacon, Beaujade, Belle de Boskoop, Big Time, Blushing Golden, Braeburn, Bramley's Seedling, Britegold, Champion, Chenango, Chieftain, Cleopatra, Connel Red, Coromandel Red, Cortland, Cox's Orange Pippin, Crispin, Criterion, Dayton, Delicious (including Red Delicious), Democrat, Discovery, Dorsett Golden, Dulcet, Earliblaze, Earlidel, Earligold, Early Cortland, Ein Shemer, Elstar, Empire, Empress, Fameuse, Fiesta, Florina, Freedom, Fuji, Gala, Galaxy, Geneva Early, Gingergold, Gloster, Golden Russet, Golden Delicious, Golden Supreme, Granny Smith, Gravenstein, Greensleeves, Grimes Golden, Haralson, Hauguan, Haushuai, Honeygold, Hatsuaki, Himekami, Hokuto, Idared, Iwakami, James Grieve, Jerseymac, Jonafree, Jonagold, Jonagored, Jonalicious, Jonamac, Jonared, Jonasty, Jonathan, Jonnee, Jored, Karmijn, Kitakami, Laxton's Superb, Liberty, Lodi, Lurared, Lysgolden, Macoun, Maigold, McShay, McIntosh, Melrose, Mollies Delicious, Monroe, Northern Spy, Northwestern Greening, Nova Easygro, Novamac, Orin, Ozark Gold, Paulared, Pink Lady, Prima, Prime Gold, Primicia, Princessa, Priscilla, PureGold, Ralls Janet, Raritan, Red Baron, Redchief, Regent, Reine des Reinettes, Reinette du No. 22 (nucleotide 43–82); SEQ. ID. No. 23 (nucleotide 83–122) and the lower strand (antisense strand) formed by three oligonucleotides; SEQ. ID. No. 24, SEQ. ID. No. 25, and SEQ. ID. No. 26. The sequence of each fragment is shown below. The first choice for an intermediate vector was pMON530 so the synthetic gene was designed to begin with BglII and end with EcoRI cohesive ends. The two restriction sites are shown in bold face:

| | | |
|---|---|---|
| 5' | GATCTATGCCGAAATGGAAAGTCTTCAAGAAAATTGAAAAAG 3' | SEQ. ID. No. 21 |
| 5' | TCGGTCGCAACATTCGAAACGGTATTGTCAAGGCTGGACC 3' | SEQ. ID. No. 22 |
| 5' | AGCGATCGCGGTTTTAGGCGAAGCCAAAGCGCTAGGATAA 3' | SEQ. ID. No 23 |
| 5' | AATGTTGCGACCGACTTTTTCAATTTTCTTGAAGACTTTCCAT TTCGGCATA | SEQ. ID. No. 24 |
| 5' | AAAACCGCGATCGCTGGTCCAGCCTTGACAATACCGTTTCG 3' | SEQ. ID. No. 25 |
| 5' | AATTCTTATCCTAGCGCTTTGGCTTCGCCT 3' | SEQ. ID. No. 26 |

Canada, R.I. Greening, Rome Beauty, Rubinette, Sansa, Sayaka, Sekai-ichi, Senshu, Shamrock, Shizuka, Sir Prize, Smoothee, Spartan, Stayman, Winesap, Spigold, Splendor, State Fair, Sturmer Pippin, Summerdel, SummerRed, Summer Treat, Sundowner, Sunrise, Sweet Sixteen, Takana, Tompkins King, Tsugaru, Twenty Ounce, Tolman Sweet, Tydeman's Early Worcester, Viking, Vista Bella, Wealthy, Williams Pride, Winesap, Winter Banana, Wolf River, Worcester Pearmain, Yataka, Yellow Newtown, Yoko, York Imperial, 2085, and other Gala X Splendor clones.

Suitable apple rootstocks include M.7, M.9, M.26, M.27, MM.106, MM.111, Merton 793, Maruba kaido, Budagovsky 9, Mark, Ottawa 3, and seedling (i.e. a rootstock propagated from a seed of unknown parentage).

Suitable European pears (*Pyrus communis*) include Conference, Williams Bon Cretien (Bartlett), Dr. Jules Guyot (Limonera), Blanquilla (*Spadona Estiva*), Coscia (Ercolini), Abate Fetel, d'Anjou, Beurré Bosc, Comice, Packham's Triumph, and Passe Crassane.

Suitable Asian pears (*P. pyrifolia*) include Shinseiki, 20th Century, Hosui, Shinko, Chojuro, Kosui, and Niitaka.

Suitable pear rootstocks include *Pyrus callervana, P. betulaefolia* (Reimer's), Quince, Old Home X Farmingdale, Old Home, and seedling.

The following examples are provided to illustrate embodiments of the present invention but are by no means intended to limit its scope.

EXAMPLES

Example 1
Formation of Plasmid Vector pLDB10

The plasmid vector pLDB10, having a gene encoding for the SB-37 lytic protein, was prepared by the process of the Destefano Beltran Thesis, which is hereby incorporated by reference. Essentially this approach requires the enzymatic ligation of synthetic complimentary oligonucleotides with a plasmid.

The gene sequence was divided into six fragments. The upper-strand (coding/strand) was composed of three oligonucleotides; SEQ. ID. No. 21 (nucleotide 1–42); SEQ. ID.

The 6 fragments, having the designation SEQ. ID. Nos. 21–26, are ligated by T4 DNA ligase to form a 120 bp SB-37 fragment.

Figure 10:
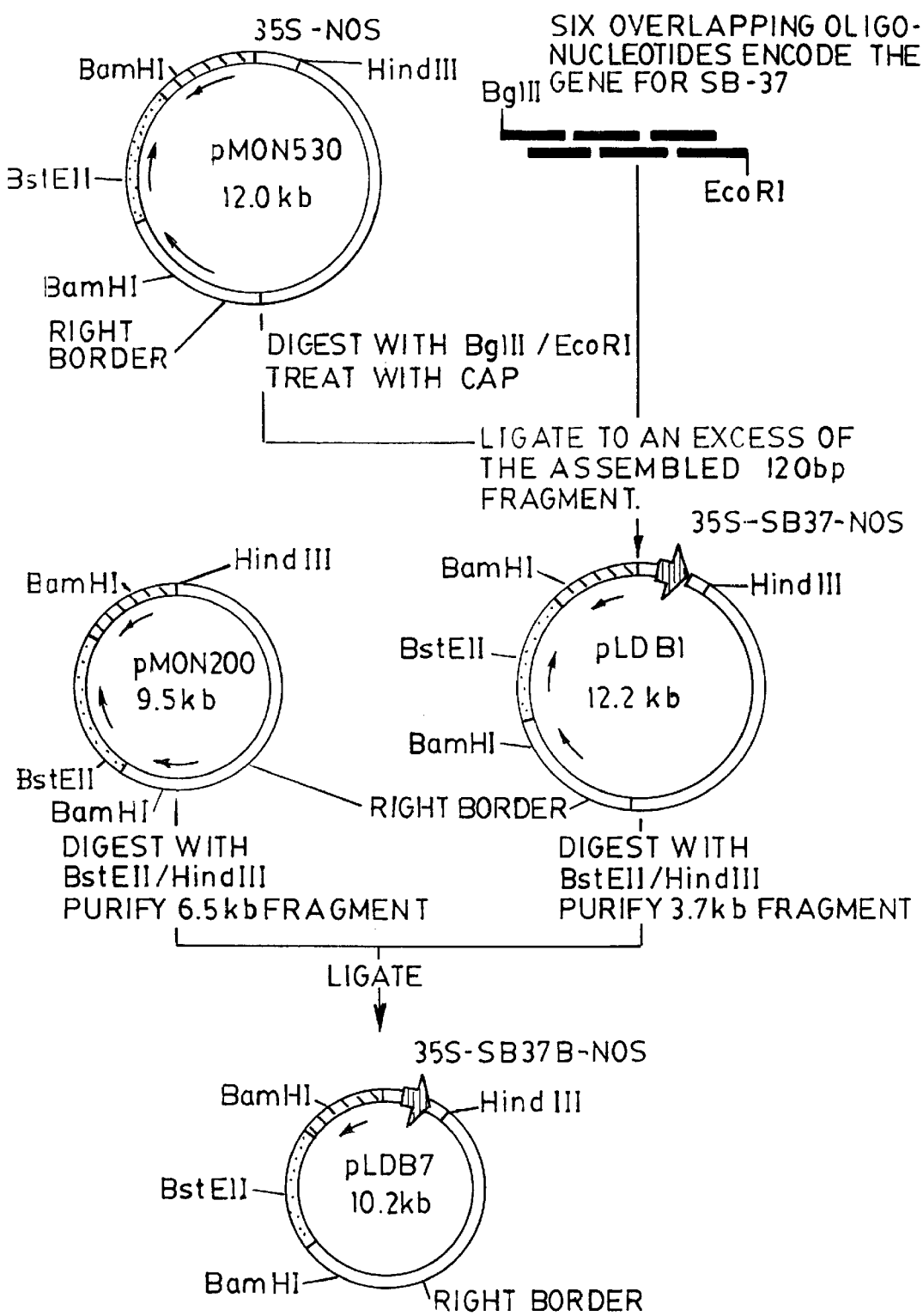
FIG. 10 is a schematic drawing showing the steps of forming plasmid vector pLDB7.

The steps of forming pLDB7 are shown in FIG. 10 and described below. After digesting the plasmid vector pMON530 with BglII and EcoRI and, then, treating with Calf Intestinal Alkaline Phosphatase ("CAP"), the six overlapping oligonucleotides which encode the gene for SB-37 are ligated into that fragment to form plasmid vector pLDB1. Plasmid vector pLDB1 is then digested with BstEII and HindIII, and the resulting 3.7 kb fragment is recovered. After digesting the plasmid vector pMON200 with BstEII and HindIII and recovering the resulting 6.5 Kb fragment, that fragment is ligated to the 3.7 Kb fragment derived from plasmid vector pLDB1 to form plasmid vector pLDB7.

Figure 11:
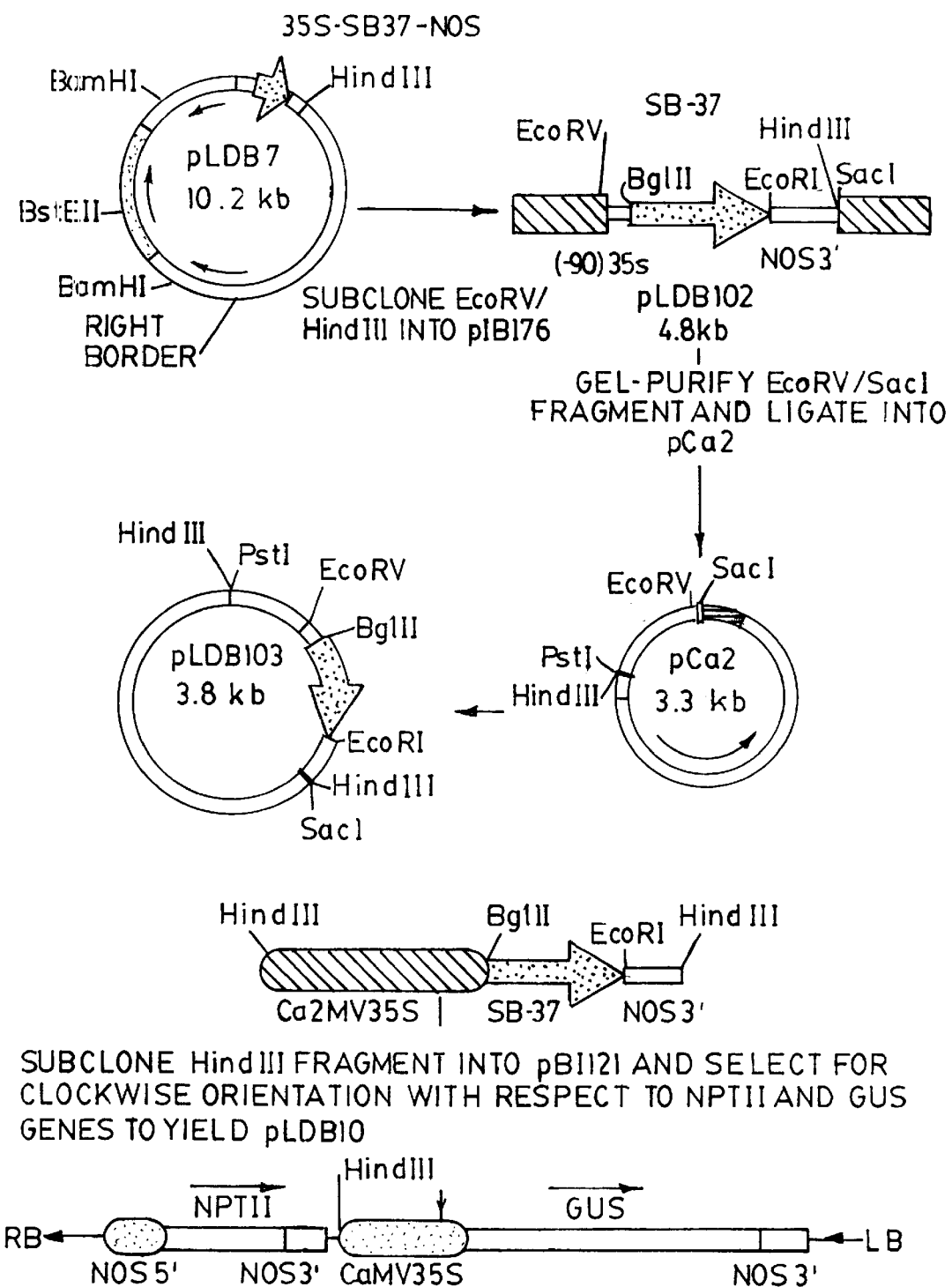
FIG. 11 is a schematic drawing showing the steps of forming plasmid vector pLDB10.

Plasmid vector pLDB10 is formed from plasmid vector pLDB7 by the sequence of steps shown in FIG. 11. This process is carried out to ensure a ten-fold higher level of expression by constructing a chimeric SB-37 gene with a variant of the CaMV35S promoter. In this process, plasmid vector pLDB7 is digested with EcoRV and SacI to release a truncated (-90)CaMV35S-SB37-NOS3' fragment that was subcloned into plasmid vector pLDB102. After digesting plasmid vector pLDB102 with EcoRV and SacI, the EcoRV/SacI fragment is ligated into plasmid vector pCa2 to form plasmid vector pLDB103. The HindIII fragment from plasmid vector pLDB103 was then subcloned into plasmid vector pBI121 to form plasmid vector pLDB10.

Example 2
Formation of plasmid vector pLDB14

As shown in FIG. 12, from the Destefano Beltran Thesis, which is hereby incorporated by reference, plasmid vector pLDB1 (formed in Example 1) was digested with BglII and EcoRI and ligated with the plasmid vector pUC19 after it is digested with HincII and treated with CAP. The resulting plasmid vector pLDB101 was then treated with BamHI and PstI to excise the gene encoding for SB-37 and then cloned into the BamHI/PstI sites of plasmid vector pIG1 to form plasmid vector pLDB141. A chimeric PiII5'-PiII3' cassette was then excised from the plasmid vector pLDB141 using two HindIII sites and inserted into the respective site of plasmid vector pBI121 to yield plasmid vector pLDB14.

Example 3

Formation of plasmid vector pLDB15

As set forth in the Destefano Beltran Thesis, which is hereby incorporated by reference, the Attacin E gene is present in plasmid vector pCP521 as a complete cDNA sequence having 564 base pairs of coding sequence and 159 base pairs in the 3' non-coding region (i.e., 723 base pairs) in the PstI site of plasmid vector pBR322. The nucleotide (SEQ. ID. No. 27) and numbered amino acid (SEQ. ID No. 28) sequences of this cDNA together with a restriction map of the insert in the attacin clone pCP521 is shown in FIG. 13. The putative polyadenylation signal is underlined in this figure.

Figure 14:
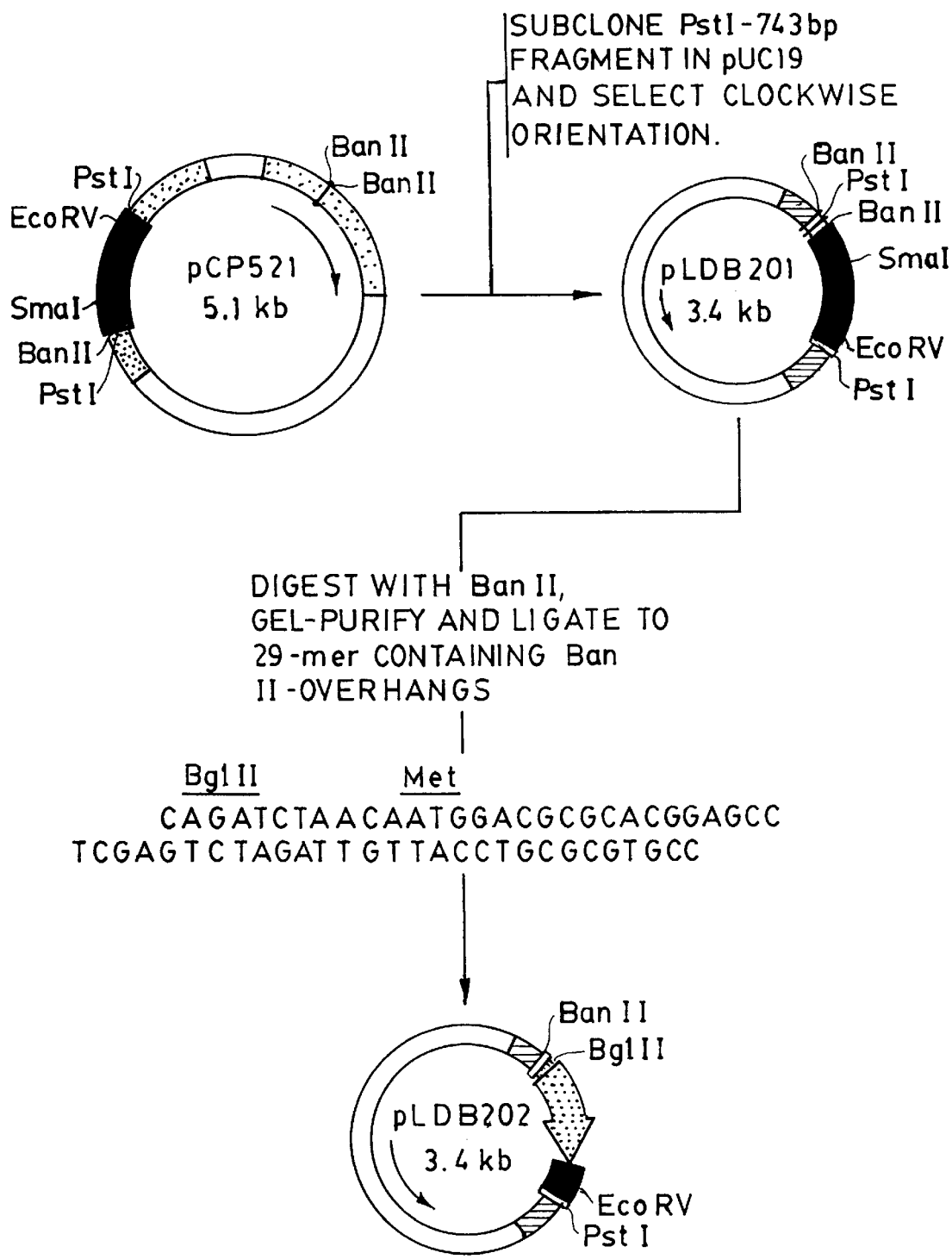
FIG. 14 is a schematic drawing showing the steps of forming plasmid vector pLDB202.

FIG. 14 is a schematic drawing of the steps used to create plasmid vector pLDB202. As shown, the PstI-723 base pair fragment from plasmid vector pCP521 was subcloned into pUC19 (see FIG. 12) such that the BanII site of pUC19 was located close to the BanII site at position 11 in the cDNA clone. The resulting plasmid vector pLDB201 was then digested with BanII and then ligated to the 29-mer oligonucleotide, containing a BglII site followed by a plant consensus AACA<u>ATG</u> sequence surrounding an initiation codon and the coding sequence for Asp1-Ala2-His3-Gly4-Ala5 with BanII overhangs, to form plasmid vector pLDB202.

Figure 15:
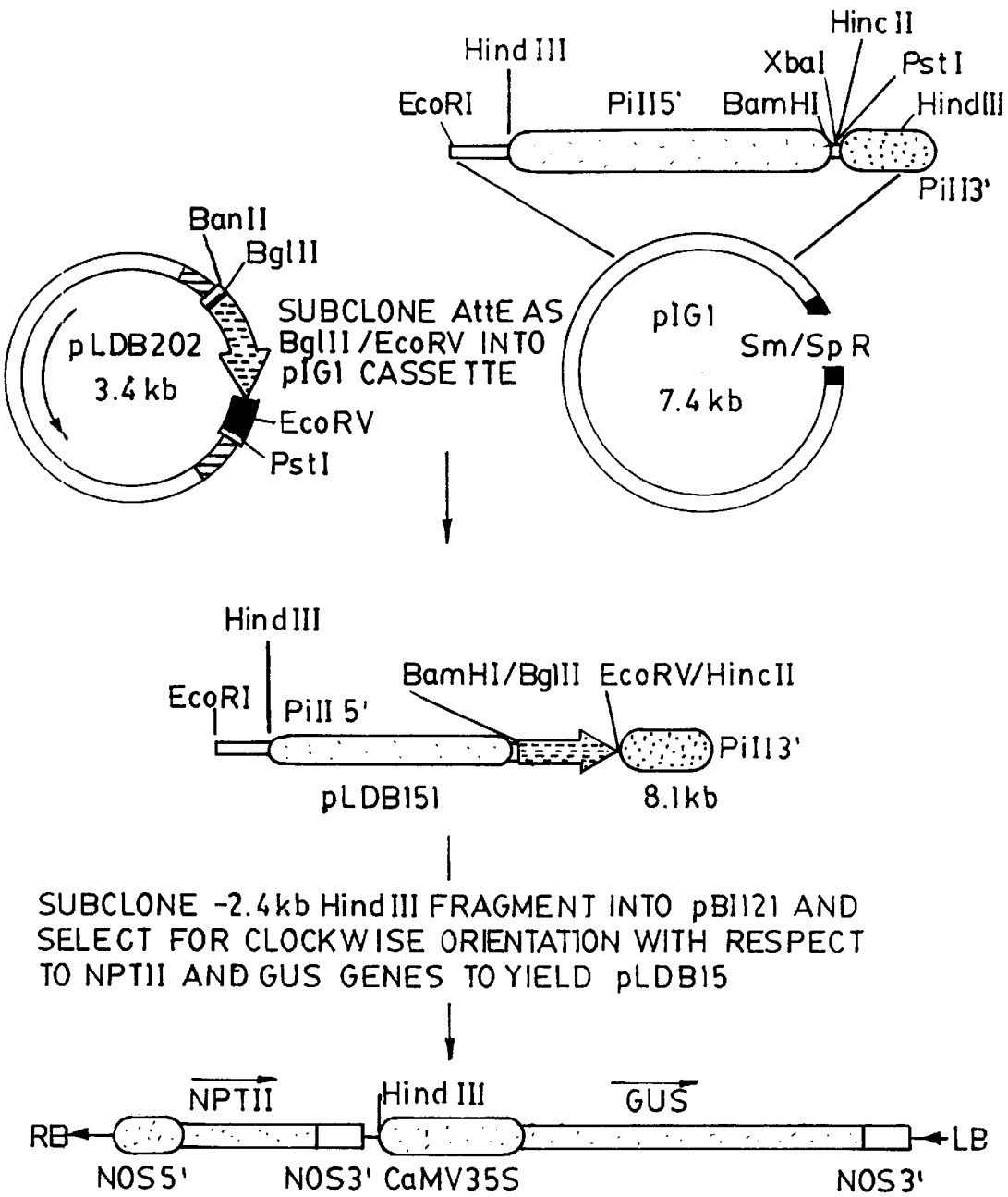
FIG. 15 is a schematic drawing showing the steps of forming plasmid vector pLDB15.

Plasmid vector pLDB202 is used to form plasmid vector pLDB15 in accordance with the schematic process drawing of FIG. 15. In this phase of the process, the Attacin E coding sequence in plasmid vector pLDB202 is excised from plasmid vector pLDB202 as a BglII/EcoRV fragment and cloned into the BamHI/HincII sites of pIG1 to form plasmid vector pLDB151. A chimeric gene fragment, located between the HindIII sites of plasmid vector pLDB151 was excised and inserted into plasmid vector pBI121 to form plasmid vector pLDB15.

Example 4

Plant Tissue Culture and Transformation with Plasmid Vectors pLDB10, pLDB14, and pLDB15.

An apple cultivar used for transformation. Methods and media used for shoot tip proliferation, and rooted-plant culture are described in J. L. Norelli et al., "Virulence of *Erwinia amylovora* Strains to *Malus sp.* Novole Plants Grown in vitro and in the Greenhouse," *Phytopathology*; 78:1292–97 (1988), which is hereby incorporated by reference except that the proliferation medium contained 1.0 mg benzyladenine/L, 0.3 mg indolebutyric acid/L, and 0.2 mg gibberellic acid ($A_3$ 90% of total gibberellins)/L.

Disarmed *A. tumefaciens* strain LBA4404 (A. Hoekema et al. "A Binary Plant Vector Strategy Based on Separation of vir and T-region of the *Agrobacterium tumefaciens* Ti-plasmid," *Nature* 303:179–80 (1983), which are hereby incorporated by reference) containing the binary vectors pBI121 (R. A. Jefferson et al., "GUS Fusions: β-glucuronidase as a Sensitive and Versatile Gene Fusion Marker in Higher Plants," *EMBO J*, 6:3901–07 (1987), which are hereby incorporated by reference), pLDB10, pLDB14, or pLDB15 of Examples 1–3 (L. Destéfano-Beltran et al., *The Molecular and Cellular Biology of the Potato*, CAB International, pp. 205–21 (1990), which are hereby incorporated by reference,) were used for plant transformation. The bacteria were grown in Kado 523 broth (C. I. Kado et al., "Selective Media for Isolation of Agrobacterium, Corynebacterium, Erwinia, Pseudomonas, and Xanthomonas," *Phytopathology*, 60:969–76 (1970), which is hereby incorporated by reference), overnight at 28° C., resuspended in 0.5X Murashige-Skoog micro- and macro-elements (T. Murashige, et al., "A Revised Medium for Rapid Growth and Bioassay with Tobacco Tissue Culture," *Physiol Plant*, 15:473–97 (1962), which is hereby incorporated by reference), pH 5.4, containing 100 μM acetosyringone, and adjusted to a density of $2 \times 10^9$ cfu/ml by measuring absorbance at 600 nm. Leaves used for transformation were harvested from 3-wk-old or 8-wk-old rooted in vitro plant cultures. The leaves were fully unfolded yet still in an active stage of leaf expansion. Leaves were sliced transversely into segments 3–5 mm wide with a scalpel, placed in *A. tumefaciens* inoculum for 5 min., blotted dry, and placed abaxial side up on regeneration medium without antibiotics. Regeneration medium was the modified $N_6$ medium containing 5 mg benzyladenine/L and 0.1 mg 1-naphthaleneacetic/L as described by M. Welander in "Plant Regeneration from Leaf and Stem Segments of Shoots Raised in vitro from Mature Apple Trees," *J. Plant Physiology* 132:738–744 (1988), which is hereby incorporated by reference. Plates were incubated in the dark for 48 hours at room temperature to allow for infection and transformation by *A. tumefaciens*. Leaf segments were then transferred to regeneration medium containing 250 μg/ml cefotaxime or 10 μg/ml paromomycin and 250 μg/ml cefotaxime. In an additional treatment, leaf segments were transferred to regeneration medium containing 40 μg/ml paromomycin and 250 μg/ml cefotaxime for 4 days and then to regeneration medium containing only cefotaxime. Leaf pieces on regeneration medium were first placed in the dark at room temperature (21°–30° C.) for 2 weeks and then placed at 40 μmol·m$^{-2}$·sec$^{-1}$, 16 h day at room temperature (21°–30° C.). In all treatments, leaf segments were transferred to fresh medium after 4 weeks.

9 weeks after inoculation with *A. tumefaciens*, all regenerating leaf segments were transferred to a baby food jar containing the same regeneration medium (50 ml) on which they were previously cultured. Four weeks later, regenerating cultures were divided into pieces containing 1 or a few meristems and were placed on proliferation medium containing 50 μg/ml kanamycin. Shoot tips that remained green on kanamycin medium after 6 weeks were screened for GUS activity.

The presence of GUS in putative transgenic plants was determined using a fluorometric assay based on the cleavage of 4-methylumbelliferyl-β-D-glucuronide ("MUG") to 4-methylumbelliferone ("MU"), as described by R. A. Jefferson et al., "GUS Fusions: β-glucuronidase as a Sensitive and Versatile Gene Fusion Marker in Higher Plants," *EMBO J.*, 6:3901–07 (1987), which is hereby incorporated by reference. In preliminary assays 50 to 150 mg fresh weight of leaf tissue was ground in 500 μl extraction buffer (Id.). 100 μl aliquots of the leaf extracts were mixed with 100 μl of 2 mM MUG in a multiwell microtiter dish. The mixture was incubated at 37° C. overnight, and observed under ultraviolet light for fluorescence. Quantitative GUS assays were conducted as described by R. A. Jefferson (Id.) except that 20 μl aliquots were removed at sample times, four sample times were used to calculate rates of activity, and assays were run for up to 200 min. Quantitative GUS data was normalized by a log transformation. The accumulation of MU over time was linear and did not approach an asymptote or depart from linearity during the assay time period.

A histochemical assay for the localization of GUS activity was performed, as described by R. A. Jefferson et al., "GUS Fusions: β-glucuronidase as a Sensitive and Versatile Gene Fusion Marker in Higher Plants," *EMBO J.*, 6:3901–07

(1987), which is hereby incorporated by reference, except that hand sections were not fixed in formaldehyde prior to treatment with 5-Bromo-4-chloro-3-indolyl-β-D-glucuronic acid ("X-gluc").

nptII activity was assayed by evaluating the ability of in vitro grown shoot tips to root in the presence of 25 or 50 µg/ml kanamycin. A single baby food jar of rooting medium containing 5 shoot tips was the unit of replication. There were 5 to 25 jars per treatment.

To conduct a Southern analysis, plant DNA was isolated from fresh leaf tissue using a modification of the N. J. Gawel, "A modified CTAB DNA extraction procedure for Musa and Ipomoea," *Plant Mol. Biol. Rep.*, 9:262–66 (1991), which is hereby incorporated by reference, procedure. Modifications were 1) the leaf tissue-extraction buffer mixture was incubated at 37° C. for 45 min and 2) following treatment of DNA with RNAse, the DNA was treated with Proteinase K (1.5 mg/ml) at 55° C. for 90 min. 10 µg genomic DNA was digested with HindIII, separated by size through a 1% agarose gel in Tris-acetate-EDTA buffer at 1.1 V/cm for 16 hours, transferred to GeneScreenPlus (DuPont Co., Boston, Mass.) under alkaline conditions, hybridized at 65° C. in aqueous solution with 200 ηg of $^{32}$P labeled DNA probe with a specific activity $>10^9$ cpm/µg, and washed at high stringency (J. Sambrook et al., *Molecular Cloning: A Laboratory Manual*, Cold Spring Harbor Laboratory Press (2nd ed. 1989), which is hereby incorporated by reference). The attacin probe was the 2.2 kb HindIII fragment of pLDB15 and consisted of the 5' and 3' region of the proteinase inhibitor II gene from potato and the attacin gene. The GUS probe was the approximately 2.1 kb BamHI-EcoRI fragment of pBI121 and consisted of the GUS gene and the nopaline synthase terminator from *A. tumefaciens*. The nptII probe was the approximately 1.9 kb PstI fragment of pBI121 and consisted of most of the nptII gene and the nopaline synthase terminator.

Example 5
Recovery of Transgenic Plant.

A transgenic line, designated T1, was obtained that contains the gene encoding Attacin E protein. T1 was obtained from a leaf segment harvested from an 8-wk-old rooted in vitro plant culture, inoculated with LBA4404 (pLDB15), and was selected on medium containing 10 µg/ml paromomycin and 250 µg/ml cefotaxime. Although T1 was obtained from a leaf harvested from an 8-wk-old plant, a significantly higher proportion of leaf segments from 3-wk-old rooted plants regenerated (0.22) than did those from 8-wk-old plants (0.11) (F=7.98, df=1, 63). There was no significant difference in the proportion of leaf segments that regenerated when cultured on medium containing 250 µg/ml cefotaxime (0.23), 10 µg/ml paromomycin and 250 µg/ml cefotaxime (0.16), or 40 µg/ml paromomycin and 250 µg/ml cefotaxime for 4 days and then 250 µg/ml cefotaxime (0.12) (F=2.63, df=2, 62). There was no significant difference in the portion of leaf segments that yielded transgenic plants when leaves were harvested from 3-wk-old (0.0) or from 8-wk-old plants (0.0033) (F=1.17, df=1, 63); nor when leaf segments were cultured on medium containing only cefotaxime (0.0), 10 µg/ml paromomycin plus cefotaxime (0.0083), or 40 µg/ml paromomycin plus cefotaxime for 4 days and then only cefotaxime (0.0) (F=0.91, df=2, 62).

There were a high number of non-transgenic escapes that regenerated on medium containing paromomycin to select for nptII transgenic plants. Only 1 of 36 regenerants from medium with 10 µg/ml paromomycin was transgenic (2.2%), and none of 25 regenerants cultured on medium with 40 µg/ml paromomycin for 4 days were transgenic. Failure to attain a significant difference in the proportion of leaf segments that regenerated when cultured on medium with non-paromomycin versus on medium containing paromomycin indicates that the selection pressure used in this experiment was too low. Recent studies have indicated that continuous selection with 25 to 63 µg/ml paromomycin was optimal to select for nptII transgenic M.26 cells.

As shown in Table II, transgenic line T1 possessed nptII and GUS activity, while the non-transgenic line M.26 did not.

TABLE II

|  | nptII[a] | | GUS[b] |
|---|---|---|---|
|  | 25 µg/ml | 50 µg/ml |  |
| Non-transgenic line | 0% | 0% | 0.6 |
| T1 | 124% | 93% | 79.7 |

[a]Ability of tissue culture shoots to root in the presence of kanamycin. Rooting was observed after 4 weeks of cultivation on rooting media and is expressed as a percent of rooting that occurred in the absence of antibiotics (76% and 48% for Non-transgenic line and T1, respectively).
[b]Rate of MUG to MU conversion (ηmoles/min/mg fresh weight) as determined by fluorometric assay.

Analysis of variance of nptII activity indicated a significant difference between the nptII activity of the non-transgenic line and T1 (F=51.56, df=1, 146) and a significant cultivar by kanamycin concentration interaction (F=57.72, df=2, 142), indicating that the non-transgenic line and T1 responded differently to the presence of kanamycin in rooting medium. Analysis of variance of GUS activity indicated a significant difference between the GUS activity of the non-transgenic line and T1 (F=13.35, df=1, 14).

Figure 16A:
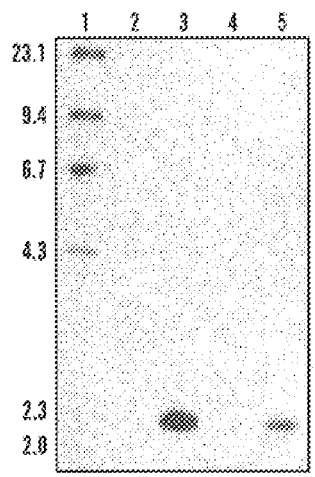
FIGS. 16A, 16B, and 16C show the Southern Analysis for the transgenic apple (T1) of the present invention hybridized with an attacin gene probe, a β-glucuronidase ("GUS") probe, and a neomycin phosphotransferase gene ("nptII") probe, respectively. In each, lambda is in lane 1, pBI121 is in lane 2, pLDB15 is in lane 3, the non-transgenic line genomic DNA is in lane 4, and T1 genomic DNA is in lane 5. The DNA in all five lanes was digested with HindIII. T1 is an Attacin E lytic protein transgenic derived from the non-transgenic line. pLDB15 contains a ca. 2400 bp HindIII fragment containing the Attacin E protein gene inserted into the HindIII site of the binary vector pBI121. The numbers at the left side of these figures indicate the size in kb of the lambda size markers. The approximate locations of the lambda size markers are drawn into lane 1 of 16B and 16C.

The Agrobacterium binary vector used in the transformation of T1, pLDB15 (L. Destéfano-Beltrán et al., The *Molecular and Cellular Biology of the Potato*, CAB International, pp. 205–21 (1990), which is hereby incorporated by reference), contains an approximately 2400 bp fragment inserted in the HindIII site of pBI121 (R. A. Jefferson et al., "GUS Fusions: β-glucuronidase as a Sensitive and Versatile Gene Fusion Marker in Higher Plants," *EMBO J.* 6:3091–07 (1987), which is hereby incorporated by reference) (FIG. 15). This insert contains 1.3 kb of the 5' region of the proteinase inhibitor II gene from potato, a 640 bp Attacin E gene, and approximately 300 bp of the 3' region of the proteinase inhibitor II gene. The ordered arrangement of pLDB15 T-DNA is right T-DNA border, nptII gene, 2400 bp Attacin E HindIII fragment, GUS gene, and left T-DNA border (FIG. 15). Since the Attacin E gene is flanked by HindIII sites on the T-DNA transferred to the plant during Agrobacterium mediated transformation, digestion of either plasmid DNA or transgenic genomic plant DNA should result in a 2400 bp fragment that hybridizes with the Attacin E gene probe. Southern hybridization analysis of T1 indicated that a ca. 2400 bp fragment from pLDB15 (FIG. 16A, lane 3) and T1 (lane 5) but not pBI121 (lane 2) or the non-transgenic line (lane 4) hybridized with the attacin gene probe (FIG. 16A).

Since the GUS gene is flanked by T-DNA left border and a HindIII site, hybridization of GUS to plasmid DNA and transgenic genomic DNA digested with HindIII should result in hybridizing fragments of different sizes. The pLDB15 DNA fragment that hybridizes with GUS gene probe should be the same size as the pBI121 hybridizing fragment (FIG. 16A). The size of the hybridizing fragment in transgenic genomic DNA will be of unknown size because it will include both T-DNA (HindIII site to T-DNA left border) and plant DNA (site of integration to next plant HindIII site). Similarly, nptII is flanked by T-DNA right border and a HindIII site and hybridization of nptII to transgenic genomic DNA digested with HindIII should result in a hybridizing fragment of different size from either plasmid DNA or that which hybridizes with GUS.

Figure 16B:
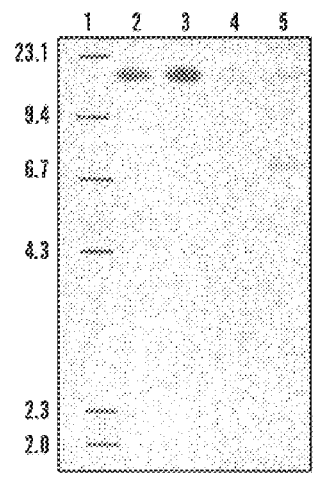

Hybridization of HindIII digested pBI121 and pLDB15 DNA indicated that a fragment the approximate size of pBI121 hybridized with the GUS gene probe (FIG. 16B, lanes 2 and 3) and the nptII probe (FIG. 16B, lanes 2 and 3). Hybridization of T1 genomic DNA indicated that a fragment of unique size (approximately 7.5 kb) hybridized with the GUS probe. A fragment the size of pBI121 also hybridized with GUS gene probe in the non-transgenic line and T1 genomic DNA samples. This band was probably due to contamination of genomic DNA samples with pBI121. Contamination of genomic DNA could have occurred by colonization of plant tissue with *A. tumefaciens* containing pBI121, contamination during DNA isolations, or migration of DNA sample during gel electrophoresis. However, despite the presence of contaminating pBI121 in plant genomic DNA samples, the presence in T1 genomic DNA of a unique fragment that hybridizes with GUS (FIG. 16B, lane 5; 7.5 kb) is proof of T1 transformation.

Figure 16C:
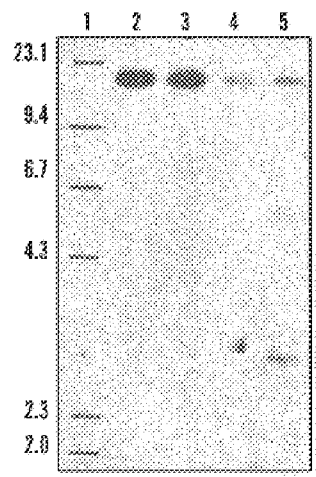

Transformation of T1 is supported by hybridization with the nptII probe (FIG. 16C). Hybridization of T1 genomic DNA with the nptII probe resulted in the hybridization of 2 fragments of unique size (approximately 5.9 and 3.4 kb) (FIG. 16C, lane 5). This may indicate a duplication of the nptII gene during the transformation process. The shadow 7.5 kb fragment (FIG. 16C, lane 5) is the GUS fragment that has hybridized with the nopaline synthase terminator common to both the GUS gene and the nptII probe. As with the GUS probe, hybridization of the non-transgenic line and T1 genomic DNA samples with the nptII probe indicate contamination with pBI121.

Example 6
Stability of Transgenic Genotype.

Since apple is vegetatively propagated and sexual crosses result in the loss of cultivar characteristics, the R0 generation of transgenic plants will most likely be used to select improved cultivars. Therefore, the stability of the R0 transgenic genotype is important.

To test the stability of T1's transgenic genotype, plants were regenerated from T1 leaf segments without any aminoglycoside selection for nptII and then evaluated for the presence of GUS and nptII marker genes. GUS activity in T1 regenerants was evaluated using a qualitative fluorometric assay for the conversion of MUG to MU, and nptII activity was evaluated by testing the ability of regenerants to root in medium containing 25 µg/ml kanamycin. Of 40 T1 regenerants evaluated, all 40 had both positive GUS and nptII activity.

Histochemical observation of T1 leaf tissue did not indicate any evidence of chimera. GUS activity was observed in all cell layers of transversely sectioned leaves. Likewise, when five successive leaves on a stem were assayed, leaves from all phyllotactic sections had GUS activity throughout.

In addition, in more than 25 successive vegetative in vitro propagations of T1 on shoot tip proliferation medium without aminoglycoside selection, there has been no apparent loss of GUS or nptII activity.

Regeneration tests, histochemical observation, and observed stability of T1 transgenic genotype after propagation and growth without selection indicate that T1 is not chimeric and is genetically stable.

Example 7
Fire blight resistance of Transgenic Apple Determined in vitro

In vitro grown plants of transgenic T1 were evaluated for their resistance to fire blight. Tissue culture plants were inoculated with *Erwinia amylovora*, the casual agent of fire blight, as previously described by Norelli et al., "Virulence of *Erwinia amylovora* Strains to *Malus sp*. Novole plants Grown in vitro and in the Greenhouse," *Phytopathology*: 78:1292–97 (1988), which is hereby incorporated by reference, except that inoculum was prepared at 5 or more various concentrations ranging from $1 \times 10^4$ to $1 \times 10^7$ cfu/ml. The inoculum dose necessary for 50% of the plants to become infected with *Erwinia amylovora* (mean ID50 in units of log10 cfu/ml) was calculated by a probit procedure (SAS, SAS Institute Inc., Cary, N.C.) and used as a measure of plant resistance. The greater the inoculum dose necessary for 50% of the plants to become infected, the more resistant the cultivar to fire blight. The non-transgenic line was included in evaluations as a susceptible standard cultivar. *Erwinia amylovora* strain Ea273 was used for inoculum. Evaluations were repeated three times and ID50 values were averaged for the three evaluations.

Figure 17:
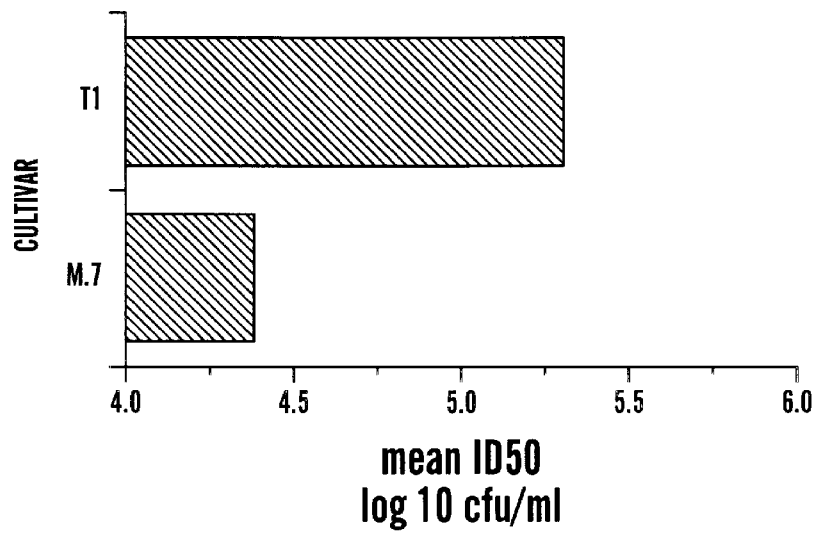
FIG. 17 shows the ID50 fire blight resistance rating for the transgenic apple cultivar (T1), and the non-transgenic line.

As seen in FIG. 17, T1, and non-transgenic line (parent cultivar) had ID50 ratings of 5.4 and 4.4 respectively, indicating that the fire blight resistance of the T1 transgenic containing the gene encoding the Attacin E protein had increased in comparison to the susceptible parent cultivar.

Example 8
Fire Blight Resistance of Transgenic Apple Plants

Figure 18:
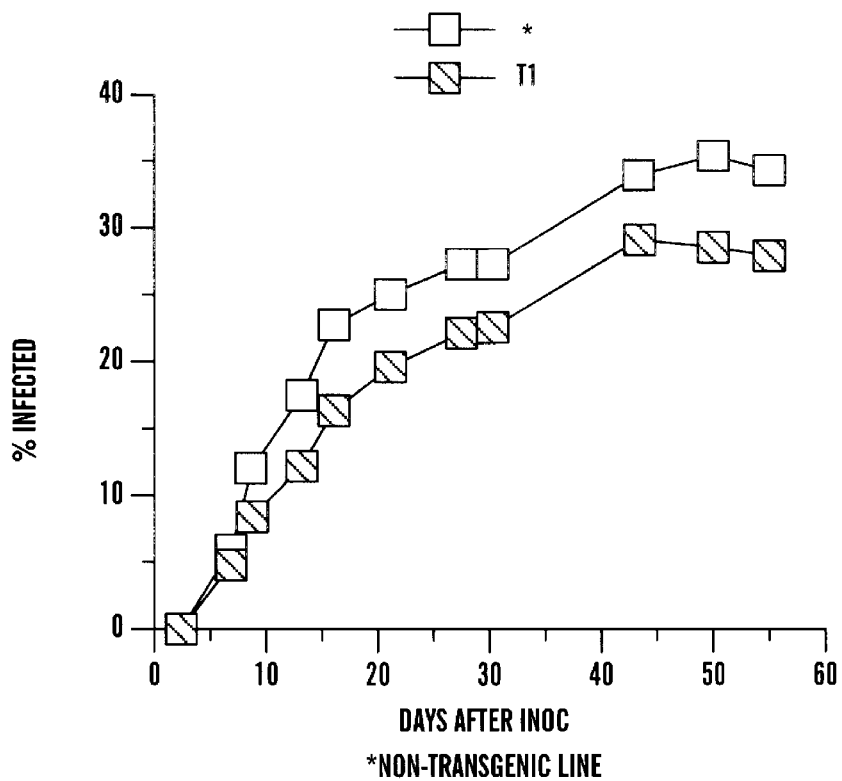
FIG. 18 shows the progress of the fire blight disease over time for the transgenic apple cultivar (T1) and the non-transgenic line parent cultivar.

In vitro propagated plants of T1 were adapted to growth in the greenhouse and grown as single shoot plants. Plants were evaluated for their fire blight resistance by determining the percent of the shoot length that developed symptoms after inoculation with *Erwinia amylovora*. Inoculations were as previously described by H. S. Aldwinckle and J. L. Preczewski, "Reaction of Terminal Shoots of Apple Cultivars to Invasion by *Erwinia amylovora*," *Phytopathology* 66:1439–44 (1976), which is hereby incorporated by reference, except that inoculum concentration was $5 \times 10^6$ cfu/ml. The cultivar non-transgenic line was included as a susceptible standard cultivar. *Erwinia amylovora* strain Ea273 was used for inoculum. FIG. 18 shows the disease progress over time in the transgenic, T1, and the parent cultivar non-transgenic line.

T1 developed less disease at a slower rate than non-transgenic line. The slopes of the disease progress curve for non-transgenic line and T1 are significantly different from day 3 thru day 16 (T=−2.37, df=124, p=0.019; based on slopes weighted to 1/x due to non-normality of x values), indicating that T1 was more resistant to fire blight.

Such rate-reducing resistance is a well known indicator of a plant's ability to suppress the rate of epidemic development, as noted in W. Fry, *Principles of Plant Disease Management*, pp. 203–04, 219–34 (1982), which is hereby incorporated by reference. Although this type of resistance can be overwhelmed by environmental conditions favorable for disease development or by large pathogen populations, it is frequently employed for disease management and can be effectively integrated with other management techniques (Id. pp. 228–231). This has been demonstrated in the control of late blight of potato caused by *Phytophthora infestans* where rate-reducing resistance was effectively combined with chemical control practices and the effect of the rate-reducing resistance used was quantified to be equivalent to 0.5 to 0.7 kilogram fungicide/hectare (W. E. Fry, "Integrated Effects of Polygenic Resistance and a Protective Fungicide on Development of Potato Late Blight," *Phytopathology* 65:908–911 (1975), which is hereby incorporated by reference, and W. E. Fry, "Quantification of General Resistance of Potato Cultivars and Fungicide Effects for Integrated Control of Potato Late Blight," *Phytopathology* 68:1650–1655 (1978), which is hereby incorporated by reference. In the case of fire blight infection of apple rootstocks, rate reducing resistance can slow disease development sufficiently for the plant to survive infection. After the initiation of infection, lesion extension will be inhibited by unfavorable conditions in the fall and winter. Rate-reducing resistance can retard lesion extension sufficiently to prevent lesions from girdling the rootstock crown. Tree loss would then be averted. This would be a significant benefit for the non-transgenic line and other susceptible apple rootstocks.

Example 9
Northern Analysis of Expression of the Attacin E. gene in T1

Expression of the gene encoding Attacin E in T1 was demonstrated by northern analysis that indicated the presence of Attacin E messenger RNA (mRNA) in T1.

Leaves were harvested from T1 plants that had been inoculated with *Erwinia amylovora*, the fire blight pathogen, 72 hours prior to leaf harvest and total RNA was isolated from leaf tissue. Since the vast majority of eucaryotic mRNAs are poly adenylated at their 3' termini, mRNA was purified from the bulk of cellular RNA by affinity chromatography on oligo(dT)-cellulose. Poly (A) RNA was then fractionated under denaturing conditions by electrophoresis though an agarose gel containing formaldehyde. Fractioned RNA was then vacuum blotted onto a nitrocellulose membrane and hybridized with radioactively labeled Attacin E DNA probe. The Attacin E probe was the 2400 bp Attacin E HindIII fragment of pLDB15.

Figure 19:
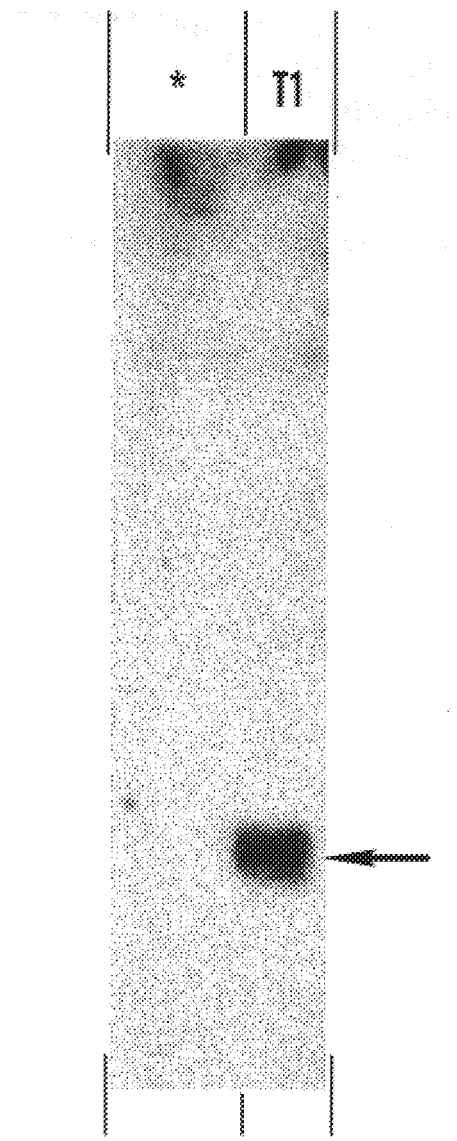
FIG. 19 shows a Northern Analysis of Expression of the Attacin E gene in T1.

Expression of Attacin E is supported by hybridization of the Attacin E probe to a fragment present in T1 mRNA that is not present in the non-transgenic line mRNA (see FIG. 19).

Example 10
Formation of Plasmid Vector pBPRS1

The plasmid vector pBPRS1 (see FIG. 20) was constructed so that genes encoding the cecropin B-like peptide Shiva-1 was fused to transit signal peptide sPR1, to allow for export of cecropins from the plant cell, and the genes were placed under the control of an enhanced 35S promoter of CaMV ($Ca_2 35S$). In brief, the gene encoding Shiva-1 was synthesized from overlapping synthetic oligomers that were cloned into a vector plasmid. Overlapping synthetic oligomers encoding the sPR1 transit signal peptide of the pathogenesis-related protein 1b from tobacco, Denecke, J., Botterman, J., and Deblaere, R., "Protein Secretion in Plant Cells can Occur via a Default Pathway," *The Plant Cell* 2:51–59 (1990), which is hereby incorporated by reference, were then fused to the 5' end of the Shiva-1 gene. DNA fragments encoding the fusion peptides (SEQ. ID. No. 17) were then subcloned into pCa2, Kay, R., Chan, A., Daly, M., and McPherson, Jr., "Duplication of CaMV35S Promoter Sequences Creates a Strong Enhancer for Plant Genes," *Science* 5 236:1299–1302 (1987), which is hereby incorporated by reference, to produce HindIII cassettes containing 5' to 3' the enhanced $Ca_2 35S$ promoter, the fusion peptide coding regions, and the nopaline synthase terminator of *Agrobacterium tumefaciens*. The cassettes were then subcloned into the HindIII site of the *A. tumefaciens* binary plasmid vector pBI121 to produce pBPRS1 (sPR1/Shiva-1 fusion).

Example 11
Isolation of Transgenic Apple Plants Containing Genes Encoding Cecropin B-like Peptides.

Transgenic apple rootstocks containing cecropin B-like lytic peptides are derived from the non-transgenic line of apple rootstock by *Agrobacterium tumefaciens* mediated gene transfer. Transgenic T2 contains a gene encoding the SB-37 peptide under the control of an enhanced CaMV 35S promoter and was selected using the binary plasmid vector pLDB10 formed in Example 1. Transgenics T3, T4, T5, T6, and T7 contain a gene encoding the Shiva-1 peptide fused to the sPR1 transit signal peptide of the pathogenesis-related protein 1b from tobacco. The gene encoding the fusion peptide is under the control of an enhanced CaMV 35S promoter. Transgenics T2 to T7 were selected using the binary plasmid vector pBPRS1, prepared in accordance with Example 10.

The methods and media used for the *A. tumefaciens* mediated gene transfer are described in Example 4, with the following exceptions.

Exception 1: Regeneration medium for T2, T5, and T7 consisted of the major and minor element salt mixture described by T. Murashige and F. Skoog, "A Revised Medium for Rapid Growth and Bioassay with Tobacco Tissue Culture," Physiol Plant 35 15:473–497 (1962), which is hereby incorporated by reference, 100 mg myo-inositol/L, 0.4 mg thiamine-HC1/L, 30 g sucrose/L, 1 mg thidiazuron/L, 0.5 mg indoleacetic acid/L, and 7 g agar/L. Regeneration medium for T3, T4, and T6 was as described for T2 except agar was replaced with 2.5 g gelrite/L.

Exception 2: The *A. tumefaciens* strain used for the transformation of T3 was EHA105.

Exception 3: *A tumefaciens* inoculum consisted of a 48 hour culture grown on medium containing 10 grams bactotryptone/L, 5 grams yeast extract/L, 5 grams sodium chloride/L, and 50 mg kanamycin/L. Inoculum was suspended as described in Example 4. Inoculum used to transform T3 was suspended in the simplified induction medium described by J. Alt-Morbe, H. Kuhlmann, and J. Schroder, "Differences in Induction of Ti Plasmid Virulence Genes virG and virD, and Continued Control of virD Expression by Four External Factors," *Molecular Plant Microbe Interactions* 2:301–308, which is hereby incorporated by reference.

Exception 4: Cocultivation medium consisted of regeneration medium plus 100 µM acetosyringone and 1 mM betaine phosphate.

Exception 5: During the cocultivation of T3, inoculated leaf pieces were incubated in the dark for 72 hours at room temperature, not 48 hours, to allow for infection and transformation by *A. tumefaciens*.

Exception 6: After cocultivation, treated leaf segments were transferred to regeneration medium containing: for T2, 250 µg cefotaxime/ml and 20 µg paromomycin/ml; for T3, 350 µg cefotaxime/ml and 100 µg kanamycin/ml; for T4 and T6, 250 µg cefotaxime/ml and 40 µg paromomycin/ml; and for T5 and T7, 250 µg cefotaxime/ml and 100 µg kanamycin/ml.

Following regeneration of meristematic tissue from treated leaf pieces, meristems were transfered to a modified regeneration medium containing Murashige and Skoog major and minor element salt mixture, 100 mg myo-inositol/L, 0.4 mg thiamine-HCI/L, 30 g sucrose/L, 1 mg benzyladenine/L, 0.5 mg naphthaleneacetic acid/L, and 7 g agar/L and incubated under high light (40 to 60 µmol/m2/sec) at 22° C. for one month. Meristems were then transferred to the proliferation medium described by J. L. Norelli et al., "Virulence of *Erwinia amylovora* Strains to *Malus sp*, Novole Plants Grown in vitro and in the Greenhouse," *Phytopathology* 78:1292–97 (1988), which is hereby incorporated by reference, containing 100 µg paromomycin/ml.

Shoots that grew on this medium were harvested and screened for beta-glucuronidase (GUS) activity.

The presence of GUS was determined using a fluorometric assay based on the cleavage of 4-methylumbelliferl-β-D-glucuronide (MUG) to 4-methylumbelliferone. 50 to 150 mg fresh weight of leaf tissue was ground in 500 μl of the extraction buffer described by R. A. Jefferson et al., "GUS Fusions: β-glucuronidase as a Sensitive and Versatile Gene Fusion Marker in Higher Plants," *EMBO J*. 6:3901, which is hereby incorporated by reference. 50 μl aliquots of the leaf extracts were mixed with 50 μl of 2 mM MUG in a multiwell microtiter dish. The mixture was incubated at 37° C. overnight, and observed under ultraviolet light for fluorescence. Transgenics were identified and propagated from shoot tips that resulted in positive GUS activity. Only one transgenic was selected from a single treated leaf piece.

Although the invention has been described in detail for the purpose of illustration, it is understood that such detail is solely for that purpose, and variations can be made therein by those skilled in the art without departing from the spirit and scope of the invention which is defined by the following claims.

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH: 396 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:1:

| | | | | | | |
|---|---|---|---|---|---|---|
| TGCCGTTCGC | AGTTCGCTTT | GCATTGCGAT | GCGAAACGTT | TCACGAGATG | CGGGTTAGTG | 60 |
| CAGGAGCTTA | GGAGACGAGG | CTTCGATGAA | ACTTTGATGA | GTAACTGGGT | CTGCCTTGTC | 120 |
| GAGAACGAAA | GCGGACGGTT | TACCGATAAA | ATCGGTAAAG | TTAACAAGAA | CGGATCTCGA | 180 |
| GACTACGGCC | TCTTCCAGAT | CAATGACAAA | TACTGGTGCA | GTAAGGATC | CACTCCTGGA | 240 |
| AAGGATTGCA | ACGTGACTTG | TAATCAGCTA | CTGACTGACG | ACATTAGCGT | GGCAGCTACG | 300 |
| TGCGCGAAGA | AGATTTACAA | ACGCCACAAG | TTTGACGCTT | GGTACGGATG | GAAAAATCAC | 360 |
| TGTCAACATG | GACTGCCAGA | TATTAGCGAC | TGTTAG | | | 396 |

( 2 ) INFORMATION FOR SEQ ID NO:2:

( i ) SEQUENCE CHARACTERISTICS:
        ( A ) LENGTH: 131 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:2:

| | | | | | | | | | | | | | | |
|---|---|---|---|---|---|---|---|---|---|---|---|---|---|---|
| Cys | Arg | Ser | Gln | Phe | Ala | Leu | His | Cys | Asp | Ala | Lys | Arg | Phe | Thr | Arg |
| 1 | | | | 5 | | | | | 10 | | | | | 15 | |
| Cys | Gly | Leu | Val | Gln | Glu | Leu | Arg | Arg | Arg | Gly | Phe | Asp | Glu | Thr | Leu |
| | | | 20 | | | | | 25 | | | | | 30 | | |
| Met | Ser | Asn | Trp | Val | Cys | Leu | Val | Glu | Asn | Glu | Ser | Gly | Arg | Phe | Thr |
| | | 35 | | | | | 40 | | | | | 45 | | | |
| Asp | Lys | Ile | Gly | Lys | Val | Asn | Lys | Asn | Gly | Ser | Arg | Asp | Tyr | Gly | Leu |
| | 50 | | | | | 55 | | | | | 60 | | | | |
| Phe | Gln | Ile | Asn | Asp | Lys | Tyr | Trp | Cys | Ser | Lys | Gly | Ser | Thr | Pro | Gly |
| 65 | | | | | 70 | | | | | 75 | | | | | 80 |
| Lys | Asp | Cys | Asn | Val | Thr | Cys | Asn | Gln | Leu | Leu | Thr | Asp | Asp | Ile | Ser |
| | | | | 85 | | | | | 90 | | | | | 95 | |

|   |   |   |   |   |   |   |   |   |   |   |   |   |   |   |
|---|---|---|---|---|---|---|---|---|---|---|---|---|---|---|
| Val | Ala | Ala | Thr<br>100 | Cys | Ala | Lys | Lys | Ile<br>105 | Tyr | Lys | Arg | His | Lys<br>110 | Phe | Asp |
| Ala | Trp | Tyr<br>115 | Gly | Trp | Lys | Asn | His<br>120 | Cys | Gln | His | Gly | Leu<br>125 | Pro | Asp | Ile |
| Ser | Asp<br>130 | Cys |

( 2 ) INFORMATION FOR SEQ ID NO:3:

( i ) SEQUENCE CHARACTERISTICS:
        ( A ) LENGTH: 586 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:3:

```
AGTCCCGCTG  TGTGTACGAC  ACTGGCAACA  TGAGGTCTTT  GCTAATCTTG  GTGCTTTGCT        60
TCCTGCCCCT  GGCTGCTCTG  GGGAAAGTCT  TTGGACGATG  TGAGCTGGCA  GCGGCTATGA       120
AGCGTCACGG  ACTTGATAAC  TATCGGGGAT  ACAGCCTGGG  AAACTGGGTG  TGTGTTGCAA       180
AATTCGAGAG  TAACTTCAAC  ACCCAGGCTA  CAAACCGTAA  CACCGATGGG  AGTACCGACT       240
ACGGAATCCT  ACAGATCAAC  AGCCGCTGGT  GGTGCAACGA  TGGCAGGACC  CCAGGCTCCA       300
GGAACCTGTG  CAACATCCCG  TGCTCAGCCC  TGCTGAGCTC  AGACATAACA  GCGAGCGTGA       360
ACTGCGCGAA  GAAGATCGTC  AGCGATGGAA  ACGGCATGAG  CGCGTGGGTC  GCCTGGCGCA       420
ACCGCTGCAA  GGGTACCGAC  GTCCAGGCGT  GGATCAGAGG  CTGCCGGCTG  TGAGGAGCTG       480
CCGCACCCGG  CCCGCCCGCT  GCACAGCCGG  CCGCTTTGCG  AGCGCGACGC  TACCCGCTTG       540
GCAGTTTTAA  ACGCATCCCT  CATTAAAACG  ACTATACGCA  AACGCC                      586
```

( 2 ) INFORMATION FOR SEQ ID NO:4:

( i ) SEQUENCE CHARACTERISTICS:
        ( A ) LENGTH: 147 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:4:

|   |   |   |   |   |   |   |   |   |   |   |   |   |   |   |   |
|---|---|---|---|---|---|---|---|---|---|---|---|---|---|---|---|
| Met<br>1 | Arg | Ser | Leu | Leu<br>5 | Ile | Leu | Val | Leu | Cys<br>10 | Phe | Leu | Pro | Leu | Ala<br>15 | Ala |
| Leu | Gly | Lys | Val<br>20 | Phe | Gly | Arg | Cys | Glu<br>25 | Leu | Ala | Ala | Ala | Met<br>30 | Lys | Arg |
| His | Gly | Leu<br>35 | Asp | Asn | Tyr | Arg | Gly<br>40 | Tyr | Ser | Leu | Gly | Asn<br>45 | Trp | Val | Cys |
| Val | Ala<br>50 | Lys | Phe | Glu | Ser | Asn<br>55 | Phe | Asn | Thr | Gln | Ala<br>60 | Thr | Asn | Arg | Asn |
| Thr<br>65 | Asp | Gly | Ser | Thr | Asp<br>70 | Tyr | Gly | Ile | Leu | Gln<br>75 | Ile | Asn | Ser | Arg | Trp<br>80 |
| Trp | Cys | Asn | Asp | Gly<br>85 | Arg | Thr | Pro | Gly | Ser<br>90 | Arg | Asn | Leu | Cys | Asn<br>95 | Ile |
| Pro | Cys | Ser | Ala | Leu<br>100 | Leu | Ser | Ser | Asp | Ile<br>105 | Thr | Ala | Ser | Val | Asn<br>110 | Cys |
| Ala | Lys | Lys<br>115 | Ile | Val | Ser | Asp | Gly<br>120 | Asn | Gly | Met | Ser | Ala<br>125 | Trp | Val | Ala |
| Trp | Arg | Asn | Arg | Cys | Lys | Gly | Thr | Asp | Val | Gln | Ala | Trp | Ile | Arg | Gly |

|  | 130 | 135 | 140 |

Cys Arg Leu
145

( 2 ) INFORMATION FOR SEQ ID NO:5:

( i ) SEQUENCE CHARACTERISTICS:
        ( A ) LENGTH: 570 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:5:

| | | | | | |
|---|---|---|---|---|---|
| GACGCGCACG | GAGCCCTTAC | GCTCAACTCC | GATGGTACCT | CTGGTGCTGT | GGTTAAAGTA | 60 |
| CCCTTTGCTG | GTAACGACAA | GAATATAGTA | AGCGCTATCG | GTTCCGTAGA | CTTAACTGAT | 120 |
| AGGCAGAAAC | TAGGCGCTGC | AACCGCTGGA | GTGGCACTGG | ATAATATAAA | CGGTCACGGA | 180 |
| CTAAGTCTCA | CGGATACACA | CATCCCCGGG | TTCGGAGACA | AGATGACAGC | AGCCGGCAAA | 240 |
| GTGAATGTCT | TCCACAATGA | TAACCACGAC | ATCACAGCGA | AGGCTTTCGC | CACCAGAAAC | 300 |
| ATGCCGGATA | TTGCTAATGT | ACCTAATTTC | AACACTGTCG | GTGGCGGAAT | AGACTATATG | 360 |
| TTCAAAGATA | AGATTGGTGC | ATCTGCGAGC | GCCGCTCACA | CGGACTTTAT | CAATCGCAAC | 420 |
| GACTACTCTC | TTGACGGGAA | ACTGAACCTC | TTCAAGACTC | CTGATACCTC | GATTGATTTC | 480 |
| AACGCCGGTT | TCAAGAAGTT | CGATACACCT | TTCATGAAGT | CCTCTTGGGA | GCCTAACTTC | 540 |
| GGATTCTCAC | TTTCTAAATA | TTTCTGATTA | | | | 570 |

( 2 ) INFORMATION FOR SEQ ID NO:6:

( i ) SEQUENCE CHARACTERISTICS:
        ( A ) LENGTH: 188 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:6:

Asp Ala His Gly Ala Leu Thr Leu Asn Ser Asp Gly Thr Ser Gly Ala
1               5                   10                  15

Val Val Lys Val Pro Phe Ala Gly Asn Asp Lys Asn Ile Val Ser Ala
            20                  25                  30

Ile Gly Ser Val Asp Leu Thr Asp Arg Gln Lys Leu Gly Ala Ala Thr
        35                  40                  45

Ala Gly Val Ala Leu Asp Asn Ile Asn Gly His Gly Leu Ser Leu Thr
    50                  55                  60

Asp Thr His Ile Pro Gly Phe Gly Asp Lys Met Thr Ala Ala Gly Lys
65                  70                  75                  80

Val Asn Val Phe His Asn Asp Asn His Asp Ile Thr Ala Lys Ala Phe
                85                  90                  95

Ala Thr Arg Asn Met Pro Asp Ile Ala Asn Val Pro Asn Phe Asn Thr
                100                 105                 110

Val Gly Gly Gly Ile Asp Tyr Met Phe Lys Asp Lys Ile Gly Ala Ser
            115                 120                 125

Ala Ser Ala Ala His Thr Asp Phe Ile Asn Arg Asn Asp Tyr Ser Leu
        130                 135                 140

Asp Gly Lys Leu Asn Leu Phe Lys Thr Pro Asp Thr Ser Ile Asp Phe
145                 150                 155                 160

```
            Asn  Ala  Gly  Phe  Lys  Lys  Phe  Asp  Thr  Pro  Phe  Met  Lys  Ser  Ser  Trp
                            165                      170                      175

Glu  Pro  Asn  Phe  Gly  Phe  Ser  Leu  Ser  Lys  Tyr  Phe
                            180                      185
```

( 2 ) INFORMATION FOR SEQ ID NO:7:

( i ) SEQUENCE CHARACTERISTICS:
    ( A ) LENGTH: 37 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:7:

```
            Lys  Trp  Lys  Leu  Phe  Lys  Lys  Ile  Glu  Lys  Val  Gly  Gln  Asn  Ile  Arg
            1                   5                   10                      15

Asp  Gly  Ile  Ile  Lys  Ala  Gly  Pro  Ala  Val  Ala  Val  Val  Gly  Gln  Ala
                            20                      25                      30

Thr  Gln  Ile  Ala  Lys
                            35
```

( 2 ) INFORMATION FOR SEQ ID NO:8:

( i ) SEQUENCE CHARACTERISTICS:
    ( A ) LENGTH: 186 base pairs
    ( B ) TYPE: nucleic acid
    ( C ) STRANDEDNESS: double
    ( D ) TOPOLOGY: unknown ( i i ) MOLECULE TYPE: DNA (genomic)

( x i ) SEQUENCE DESCRIPTION: SEQ ID NO:8:

```
ATGAATTTCT  CAAGGATATT  TTTCTTCGTG  TTCGCTTTGG  TTCTGGCTTC  AACAGTTTCG       60

GCTGCACCGG  AGCCGAAATG  GAAAGTCTTC  AAGAAAATTG  AAAAAATGGG  TCGCAACATT      120

CGAAACCGTA  TTGTCAAGGC  TGGACCAGCG  ATCGCGGTTT  TAGGCGAAGC  CAAAGCGCTA      180

GGATAA                                                                     186
```

( 2 ) INFORMATION FOR SEQ ID NO:9:

( i ) SEQUENCE CHARACTERISTICS:
    ( A ) LENGTH: 61 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:9:

```
            Met  Asn  Phe  Ser  Arg  Ile  Phe  Phe  Phe  Val  Phe  Ala  Leu  Val  Leu  Ala
            1                   5                   10                      15

Ser  Thr  Val  Ser  Ala  Ala  Pro  Glu  Pro  Lys  Trp  Lys  Val  Phe  Lys  Lys
                            20                      25                      30

Ile  Glu  Lys  Met  Gly  Arg  Asn  Ile  Arg  Asn  Gly  Ile  Val  Lys  Ala  Gly
                            35                      40                      45

Pro  Ala  Ile  Ala  Val  Leu  Gly  Glu  Ala  Lys  Ala  Leu  Gly
                            50                      55                      60
```

( 2 ) INFORMATION FOR SEQ ID NO:10:

( i ) SEQUENCE CHARACTERISTICS:
    ( A ) LENGTH: 36 amino acids (B) TYPE: amino acid
(C) STRANDEDNESS: single
(D) TOPOLOGY: unknown (ii) MOLECULE TYPE: peptide (xi) SEQUENCE DESCRIPTION: SEQ ID NO:10:

Trp Asn Pro Phe Lys Glu Leu Glu Lys Val Gly Gln Arg Val Arg Asp
1               5                   10                  15

Ala Val Ile Ser Ala Gly Pro Ala Val Ala Thr Val Ala Asn Ala Thr
                20                  25                  30

Ala Leu Ala Lys
            35

(2) INFORMATION FOR SEQ ID NO:11:

(i) SEQUENCE CHARACTERISTICS:
(A) LENGTH: 37 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:11:

Met Pro Arg Trp Arg Leu Phe Arg Arg Ile Asp Arg Val Gly Lys Gln
1               5                   10                  15

Ile Lys Gln Ile Leu Arg Ala Gly Pro Ala Ile Ala Leu Val Gly Asp
                20                  25                  30

Ala Arg Ala Val Gly
            35

(2) INFORMATION FOR SEQ ID NO:12:

(i) SEQUENCE CHARACTERISTICS:
(A) LENGTH: 38 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:12:

Met Pro Lys Trp Lys Val Phe Lys Lys Ile Glu Lys Val Gly Arg Asn
1               5                   10                  15

Ile Arg Asn Gly Ile Val Lys Ala Gly Pro Ala Ile Ala Val Leu Gly
                20                  25                  30

Glu Ala Lys Ala Leu Gly
            35

(2) INFORMATION FOR SEQ ID NO:13:

(i) SEQUENCE CHARACTERISTICS:
(A) LENGTH: 210 base pairs
(B) TYPE: nucleic acid
(C) STRANDEDNESS: double
(D) TOPOLOGY: unknown (ii) MOLECULE TYPE: DNA (genomic)

(xi) SEQUENCE DESCRIPTION: SEQ ID NO:13:

ATGAACTTTT CTAGGATCTT CTTTTTCGTG TTCGCTCTTG TTCTCGCCTT GTCCACTGTG        60

TCTGCCGCTC CTGACATGCC GCGCTGGCGT CTGTTCCGCC GTATCGACCG TGTTGGCAAA       120

CAGATCAAAC AGGGTATCCT GCGTGCTGGC CCGGCTATCG CTCTGGTTGG CGACGCCCGC       180

GCAGTTGGTT GAGAATTCGC TAGCAAGCTT 210

( 2 ) INFORMATION FOR SEQ ID NO:14:

( i ) SEQUENCE CHARACTERISTICS:
        ( A ) LENGTH: 63 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:14:

```
Met Asn Phe Ser Arg Ile Phe Phe Phe Val Phe Ala Leu Val Leu Ala
 1               5                  10                  15
Leu Ser Thr Val Ser Ala Ala Pro Asp Met Pro Arg Trp Arg Leu Phe
            20                  25                  30
Arg Arg Ile Asp Arg Val Gly Lys Gln Ile Lys Gln Gly Ile Leu Arg
        35                  40                  45
Ala Gly Pro Ala Ile Ala Leu Val Gly Asp Ala Arg Ala Val Gly
    50                  55                  60
```

( 2 ) INFORMATION FOR SEQ ID NO:15:

( i ) SEQUENCE CHARACTERISTICS:
        ( A ) LENGTH: 207 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:15:

ATGAACTTTT CTAGGATCTT CTTTTTCGTG TTCGCTCTTG TTCTCGCCTT GTCCACTGTG 60
TCTGCCGCTC CTGAGCCGAA ATGGAAAGTC TTCAAGAAAA TTGAAAAAGT CGGTCGCAAC 120
ATTCGAAACG GTATTGTCAA GGCTGGACCA GCGATCGCGG TTTTAGGCGA AGCCAAAGCG 180
CTAGGATAAG AATTCGCTAG CAAGCTT 207

( 2 ) INFORMATION FOR SEQ ID NO:16:

( i ) SEQUENCE CHARACTERISTICS:
        ( A ) LENGTH: 62 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:16:

```
Met Asn Phe Ser Arg Ile Phe Phe Phe Val Phe Ala Leu Val Leu Ala
 1               5                  10                  15
Leu Ser Thr Val Ser Ala Ala Pro Glu Pro Lys Trp Lys Val Phe Lys
            20                  25                  30
Lys Ile Glu Lys Val Gly Arg Asn Ile Arg Asn Gly Ile Val Lys Ala
        35                  40                  45
Gly Pro Ala Ile Ala Val Leu Gly Glu Ala Lys Ala Leu Gly
    50                  55                  60
```

( 2 ) INFORMATION FOR SEQ ID NO:17:

( i ) SEQUENCE CHARACTERISTICS:
        ( A ) LENGTH: 216 base pairs
        ( B ) TYPE: nucleic acid
        ( C ) STRANDEDNESS: double 5,824,861

35

36

-continued ( D ) TOPOLOGY: unknown ( i i ) MOLECULE TYPE: DNA (genomic)

( x i ) SEQUENCE DESCRIPTION: SEQ ID NO:17:

```
ATGGGATTTT TCCTTTTTTC TCAAATGCCA TCCTTCTTTC TCGTGTCCAC TCTTCTCCTT    60
TTCCTCATTA TCTCTCACTC CTCTCATGCT ACCATGCCGC GCTGGCGTCT GTTCCGCCGT   120
ATCGACCGTG TTGGCAAACA GATCAAACAG GGTATCCTGC GTGCTAGCCC GGCTATCGCT   180
CGTGTTGGCG ACGCCCGCGC AGTTGGTTGA GAATTC                              216
```

( 2 ) INFORMATION FOR SEQ ID NO:18:

( i ) SEQUENCE CHARACTERISTICS:
        ( A ) LENGTH: 69 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:18:

```
Met Gly Phe Phe Leu Phe Ser Glu Met Pro Ser Phe Phe Leu Val Ser
 1               5                  10                 15
Thr Leu Leu Leu Phe Leu Ile Ile Ser His Ser Ser Ala Ala Thr Met
            20                 25                 30
Pro Arg Trp Arg Leu Phe Arg Arg Ile Asp Arg Val Gly Lys Gln Ile
        35                 40                 45
Lys Gln Gly Ile Leu Arg Ala Gly Pro Ala Ile Ala Leu Val Gly Asp
    50                 55                 60
Ala Arg Ala Val Gly
65
```

( 2 ) INFORMATION FOR SEQ ID NO:19:

( i ) SEQUENCE CHARACTERISTICS:
        ( A ) LENGTH: 213 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:19:

```
ATGGGATTTT TCCTTTTTTC TCAAATGCCA TCCTTCTTTC TCGTGTCCAC TCTTCTCCTT    60
TTCCTCATTA TCTCTCACTC CTCTCATGCT ATGCCGAAAT GGAAAGTCTT CAAGAAAATT   120
GAAAAAGTCG GTCGCAACAT TCGAAACGGT ATTGTCAAGG CTGGACCAGC GATCGCGGTT   180
TTAGGCGAAG CCAAAGCGCT AGGATAAGAA TTC                                 213
```

( 2 ) INFORMATION FOR SEQ ID NO:20:

( i ) SEQUENCE CHARACTERISTICS:
        ( A ) LENGTH: 68 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:20:

```
Met Gly Phe Phe Leu Phe Ser Glu Met Pro Ser Phe Phe Leu Val Ser
 1               5                  10                 15
Thr Leu Leu Leu Phe Leu Ile Ile Ser His Ser Ser Ala Ala Met Pro
```

```
               20                    25                        30
    Lys  Tyr  Lys  Val  Phe  Lys  Lys  Ile  Glu  Lys  Val  Gly  Arg  Asn  Ile  Arg
              35                        40                        45
    Asn  Gly  Ile  Val  Lys  Ala  Gly  Pro  Ala  Ile  Ala  Val  Leu  Gly  Glu  Ala
              50                        55                        60
    Lys  Ala  Leu  Gly
    65
```

( 2 ) INFORMATION FOR SEQ ID NO:21:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:21:

```
GATCTATGCC   GAAATGGAAA   GTCTTCAAGA   AAATTGAAAA   AG                    42
```

( 2 ) INFORMATION FOR SEQ ID NO:22:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:22:

```
TCGGTCGCAA   CATTCGAAAC   GGTATTGTCA   AGGCTGGACC                         40
```

( 2 ) INFORMATION FOR SEQ ID NO:23:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:23:

```
AGCGATCGCG   GTTTTAGGCG   AAGCCAAAGC   GCTAGGATAA                         40
```

( 2 ) INFORMATION FOR SEQ ID NO:24:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:24:

```
AATGTTGCGA   CCGACTTTTT   CAATTTTCTT   GAAGACTTTC   CATTTCGGCA   TA       52
```

( 2 ) INFORMATION FOR SEQ ID NO:25:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: unknown (i i) MOLECULE TYPE: DNA (genomic)

(x i) SEQUENCE DESCRIPTION: SEQ ID NO:25:

| AAAACCGCGA | TCGCTGGTCC | AGCCTTGACA | ATACCGTTTC | G | | 41 |
|---|---|---|---|---|---|---|

(2) INFORMATION FOR SEQ ID NO:26:

(i) SEQUENCE CHARACTERISTICS:
        (A) LENGTH: 30 base pairs
        (B) TYPE: nucleic acid
        (C) STRANDEDNESS: double
        (D) TOPOLOGY: unknown (i i) MOLECULE TYPE: DNA (genomic)

(x i) SEQUENCE DESCRIPTION: SEQ ID NO:26:

| AATTCTTATC | CTAGCGCTTT | GGCTTCGCCT | | 30 |
|---|---|---|---|---|

(2) INFORMATION FOR SEQ ID NO:27:

(i) SEQUENCE CHARACTERISTICS:
        (A) LENGTH: 723 base pairs
        (B) TYPE: nucleic acid
        (C) STRANDEDNESS: double
        (D) TOPOLOGY: unknown (i i) MOLECULE TYPE: DNA (genomic)

(x i) SEQUENCE DESCRIPTION: SEQ ID NO:27:

| GACGCGCACG | GAGCCCTTAC | GCTCAACTCC | GATGGTACCT | CTGGTGCTGT | GGTTAAAGTA | 60 |
|---|---|---|---|---|---|---|
| CCCTTTGCTG | GTAACGACAA | GAATATAGTA | AGCGCTATCG | GTTCCGTAGA | CTTAACTGAT | 120 |
| AGGCAGAAAC | TAGGCGCTGC | AACCGCTGGA | GTGGCACTGG | ATAATATAAA | CGGTCACGGA | 180 |
| CTAAGTCTCA | CGGATACACA | CATCCCCGGG | TTCGGAGACA | AGATGACAGC | AGCCGGCAAA | 240 |
| GTGAATGTCT | TCCACAATGA | TAACCACGAC | ATCACAGCGA | AGGCTTCGC | CACCAGAAAC | 300 |
| ATGCCGGATA | TTGCTAATGT | ACCTAATTTC | AACACTGTCG | GTGGCGGAAT | AGACTATATG | 360 |
| TTCAAAGATA | AGATTGGTGC | ATCTGCGAGC | GCCGCTCACA | CGGACTTTAT | CAATCGCAAC | 420 |
| GACTACTCTC | TTGACGGGAA | ACTGAACCTC | TTCAAGACTC | CTGATACCTC | GATTGATTTC | 480 |
| AACGCCGGTT | TCAAGAAGTT | CGATACACCT | TTCATGAAGT | CCTCTTGGGA | GCCTAACTTC | 540 |
| GGATTCTCAC | TTTCTAAATA | TTTCTGATTA | GTATTTAAT | TTAATTCTA | TATATATAAA | 600 |
| TTTAGATGTA | TATGTATATA | TATATATTTT | TTTTTATTA | ATATGATATC | ACTAAATGTA | 660 |
| TTTACTCCTT | CGATTATTAT | TACTTTTTTT | GTTTAAAGAA | GTCCGCCTAA | TAAAGATAAT | 720 |
| TTG | | | | | | 723 |

(2) INFORMATION FOR SEQ ID NO:28:

(i) SEQUENCE CHARACTERISTICS:
        (A) LENGTH: 188 amino acids
        (B) TYPE: amino acid
        (C) STRANDEDNESS: single
        (D) TOPOLOGY: unknown (i i) MOLECULE TYPE: peptide (x i) SEQUENCE DESCRIPTION: SEQ ID NO:28:

| Asp | Ala | His | Gly | Ala | Leu | Thr | Leu | Asn | Ser | Asp | Gly | Thr | Ser | Gly | Ala |
|---|---|---|---|---|---|---|---|---|---|---|---|---|---|---|---|
| 1 | | | | 5 | | | | | 10 | | | | | 15 | |
| Val | Val | Lys | Val | Pro | Phe | Ala | Gly | Asn | Asp | Lys | Asn | Ile | Val | Ser | Ala |
| | | | 20 | | | | | 25 | | | | | 30 | | |
| Ile | Gly | Ser | Val | Asp | Leu | Thr | Asp | Arg | Gln | Lys | Leu | Gly | Ala | Ala | Thr |

-continued

|  | 35 |  |  |  |  | 40 |  |  |  |  | 45 |  |  |  |
|---|---|---|---|---|---|---|---|---|---|---|---|---|---|---|
| Ala | Gly<br>50 | Val | Ala | Leu | Asp | Asn<br>55 | Ile | Asn | Gly | His | Gly<br>60 | Leu | Ser | Leu | Thr |
| Asp<br>65 | Thr | His | Ile | Pro | Gly<br>70 | Phe | Gly | Asp | Lys | Met<br>75 | Thr | Ala | Ala | Gly | Lys<br>80 |
| Val | Asn | Val | Phe | His<br>85 | Asn | Asp | Asn | His | Asp<br>90 | Ile | Thr | Ala | Lys | Ala<br>95 | Phe |
| Ala | Thr | Arg | Asn<br>100 | Met | Pro | Asp | Ile | Ala<br>105 | Asn | Val | Pro | Asn | Phe<br>110 | Asn | Thr |
| Val | Gly | Gly<br>115 | Gly | Ile | Asp | Tyr | Met<br>120 | Phe | Lys | Asp | Lys | Ile<br>125 | Gly | Ala | Ser |
| Ala | Ser<br>130 | Ala | Ala | His | Thr | Asp<br>135 | Phe | Ile | Asn | Arg | Asn<br>140 | Asp | Tyr | Ser | Leu |
| Asp<br>145 | Gly | Lys | Leu | Asn | Leu<br>150 | Phe | Lys | Thr | Pro | Asp<br>155 | Thr | Ser | Ile | Asp | Phe<br>160 |
| Asn | Ala | Gly | Phe | Lys<br>165 | Lys | Phe | Asp | Thr | Pro<br>170 | Phe | Met | Lys | Ser | Ser<br>175 | Trp |
| Glu | Pro | Asn | Phe<br>180 | Gly | Phe | Ser | Leu | Ser<br>185 | Lys | Tyr | Phe |  |  |  |  |

What is claimed:

1. A method of conferring resistance against fire blight to apple scion cultivars or apple rootstock cultivars comprising:

transforming apple scion cultivars or apple rootstock cultivars with a gene which encodes for a lytic protein.

2. A method according to claim 1, wherein said transforming comprises:

contacting tissue of apple scion cultivars or apple rootstock cultivars with an inoculum of a bacterium of the genus Agrobacterium, wherein the bacterium is transformed with a vector comprising the gene which encodes for a lytic protein.

3. A method according to claim 2, wherein the bacterium of the genus Agrobacterium is *Agrobacterium tumefaciens*.

4. A method according to claim 3, wherein the *Agrobacterium tumefaciens* is strain LBA4404.

5. A method according to claim 2, wherein the tissue is selected from the group consisting of leaf tissue, root tissue, meristems, and protoplasts.

6. A method according to claim 1, wherein said transforming comprises:

propelling particles at cells of apple scion cultivars or apple rootstock cultivars under conditions effective for the particles to penetrate into the cell interior and introducing a vector comprising the gene which encodes for a lytic protein into the cell interior.

7. A method according to claim 6, wherein the vector is associated with the particles, whereby the vector is carried into the cell interior together with the particles.

8. A method according to claim 6, wherein the vector surrounds the cell and is drawn into the cell interior by the particles' wake.

9. A method according to claim 1 further comprising:

regenerating the cultivars transformed with the gene which encodes for a lytic protein to form a transgenic apple tree.

10. A method according to claim 1, wherein the lytic protein is selected from the group consisting of lysozyme, cecropins, attacins, Shiva-1, and SB-37.

11. A method according to claim 10, wherein the lytic protein is Attacin E.

12. A method according to claim 1, wherein the apple rootstock is selected from the group consisting of M.7, M.9, M.26, M.27, MM.106, MM.111, Merton 793, Maruba Kaido, Budagovsky 9, Mark, Ottawa 3, and seedling.

13. A method according to claim 12, wherein the rootstock is M.26.

14. A method according to claim 2, wherein the vector is selected from the group consisting of pLDB10, pLDB15, pBPRS1, pBCCS1, pBPRB37, and pBCCB37.

15. A method according to claim 2, wherein the bacterium of the genus Agrobacterium is *Agrobacterium tumefaciens* strain LBA4404 and the rootstock is M.26.

16. A transgenic apple scion cultivar or a transgenic apple rootstock cultivar transformed with a gene which encodes for a lytic protein that imparts fire blight resistance to the cultivar.

17. A transgenic cultivar according to claim 16, wherein the lytic protein is selected from the group consisting of lysozyme, cecropins, attacins, Shiva-1, and SB-37.

18. A transgenic cultivar according to claim 17, wherein the lytic protein is Attacin E.

19. A transgenic apple cultivar according to claim 16, wherein the apple rootstock cultivar is selected from the group consisting of M.7, M.9, M.26, M.27, MM.106, MM.111, Merton 793, Maruba Kaido, Budagovsky 9, Mark, Ottawa 3, and seedling.

20. A transgenic cultivar according to claim 19, wherein the rootstock is M.26.

21. A transgenic apple tree transformed with a gene which encodes for a lytic protein that imparts fire blight resistance to the tree.

22. A transgenic tree according to claim 21, wherein the lytic protein is selected from the group consisting of lysozyme, cecropins, attacins, Shiva-1, and SB-37.

23. A transgenic tree according to claim 22, wherein the lytic protein is Attacin E.

24. A method according to claim 1, wherein the apple scion cultivar is selected from the group consisting of Delicious, Fuji, Empire, Gala, Galaxy, Gingergold, Golden Delicious, Granny Smith, Gravenstein, Idared, Jerseymac, Jonagold, Jonathan, McIntosh, Pink Lady, R.I. Greening, Rome Beauty, Sansa, Senshu, Sundowner, Twenty Ounce, York Imperial, 2085, and other Gala x Splendor clones.

25. A transgenic apple cultivar according to claim 16, wherein the apple scion cultivar is selected from the group consisting of Delicious, Fuji, Empire, Gala, Galaxy, Gingergold, Golden Delicious, Granny Smith, Gravenstein, Idared, Jerseymac, Jonagold, Jonathan, McIntosh, Pink Lady, R.I. Greening, Rome Beauty, Sansa, Senshu, Sundowner, Twenty Ounce, York Imperial, 2085, and other Gala x Splendor clones.

* * * * *